US008634903B2

(12) United States Patent
Sharma et al.

(10) Patent No.: US 8,634,903 B2
(45) Date of Patent: Jan. 21, 2014

(54) MEASURING T-WAVE ALTERNANS

(75) Inventors: Vinod Sharma, Blaine, MN (US); Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 973 days.

(21) Appl. No.: 12/610,062

(22) Filed: Oct. 30, 2009

(65) Prior Publication Data

US 2011/0105929 A1  May 5, 2011

(51) Int. Cl.
*A61B 5/0468* (2006.01)

(52) U.S. Cl.
USPC .......................................................... 600/515

(58) Field of Classification Search
USPC ......... 600/373, 374, 377, 508, 509, 515–519, 600/521, 523
See application file for complete search history.

(56) References Cited

U.S. PATENT DOCUMENTS

| | | |
|---|---|---|
| 4,374,382 A | 2/1983 | Markowitz |
| 5,117,824 A | 6/1992 | Keimel et al. |
| 5,148,812 A | 9/1992 | Verrier et al. |
| 5,265,617 A | 11/1993 | Verrier et al. |
| 5,437,285 A | 8/1995 | Verrier et al. |
| 5,545,186 A | 8/1996 | Olson et al. |
| 5,569,370 A | 10/1996 | Gomez |
| 5,755,736 A | 5/1998 | Gillberg et al. |
| 5,842,997 A | 12/1998 | Verrier et al. |
| 5,891,048 A * | 4/1999 | Nigam et al. ................. 600/521 |
| 5,921,940 A | 7/1999 | Verrier et al. |
| 6,735,466 B1 | 5/2004 | Haghighi-Mood |
| 6,823,213 B1 | 11/2004 | Norris et al. |
| 6,983,183 B2 | 1/2006 | Thiagarajan et al. |
| 7,027,867 B2 | 4/2006 | Park et al. |
| 7,136,694 B2 | 11/2006 | Hadley et al. |
| 2004/0186527 A1 | 9/2004 | Rouw et al. |
| 2005/0222510 A1 | 10/2005 | Hadley et al. |
| 2006/0116596 A1* | 6/2006 | Zhou et al. .................... 600/516 |
| 2009/0143692 A1 | 6/2009 | Brockway et al. |
| 2009/0192398 A1 | 7/2009 | Zhou et al. |

FOREIGN PATENT DOCUMENTS

| | | |
|---|---|---|
| EP | 1050271 A2 | 11/2000 |
| EP | 2030565 A1 | 3/2009 |

OTHER PUBLICATIONS

Swerdlow et al., "High Amplitude T-wave Alternans Precedes Spontaneous Ventricular Tachycardia or Fibrillation in ICD Electrograms," Heart Rhythm, vol. 5, No. 5, May 2008, pp. 670-676.
Paz et al, "Detection of 7-wave alternans using an implantable cardioverter-defibrillator," Heart Rhythm, vol. 3, No. 7, Jul. 2006, pp. 791-797.

(Continued)

*Primary Examiner* — Christopher D Koharski
*Assistant Examiner* — Frances Oropeza
(74) *Attorney, Agent, or Firm* — Michael C. Soldner

(57) ABSTRACT

An implantable medical device (IMD), such as an implantable pacemaker, cardioverter, or diagnostic device, generates an EGM signal, e.g., a far field EGM signal, samples the EGM signal to obtain a single T-wave amplitude value for each T-wave over a plurality of beats, and stores the T-wave amplitude values in memory. The IMD creates a time series of the T-wave amplitude values stored in memory, calculates the power spectral density for the times series, and selects a power spectral density of a particular frequency, e.g., 0.5 cycles per beat, as the TWA value. The IMD may periodically determine TWA values for the patient and store the values in memory. The TWA values may be presented to medical personnel, e.g., as a trend. The IMD may deliver or modify therapy, or provide an alert, based on the TWA values.

26 Claims, 15 Drawing Sheets

(56) References Cited

OTHER PUBLICATIONS

Nearing et al., "Modified moving average analysis of T-wave alternans to predict ventricular fibrillation with high accuracy," J Appl Physiol 92: 541-549, 2002.
Written Opinion from corresponding PCT Application Serial No. PCT/US2010/033366 dated Feb. 7, 2012 (6 pages).
Reply to Written Opinion dated Feb. 7, 2012, from corresponding PCT Application Serial No. PCT/US2010/033366, filed Mar. 6, 2012, (10 pages).
International Preliminary Report on Patentability from corresponding PCT Application No. PCT/US2010/033366 dated Mar. 16, 2012, (12 pages).
Search Report and Written Opinion from corresponding PCT Application Serial No. PCT/US2010/033366 dated Jul. 19, 2010 (13 pages).
Reply to Written Opinion dated Jul. 19, 2010, from international application No. PCT/US2010/033366, filed Aug. 30, 2011, 13 pp.

* cited by examiner

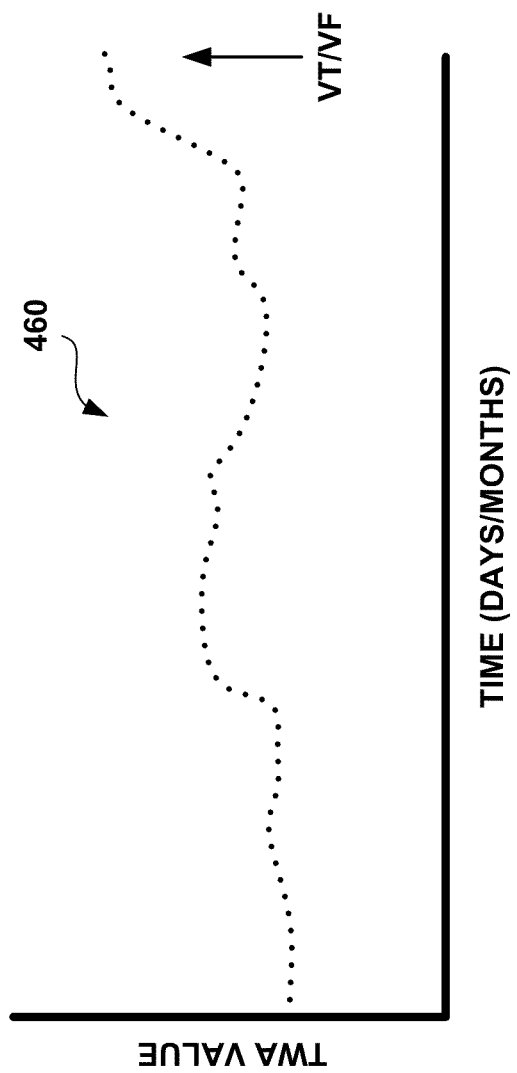

MEASURING T-WAVE ALTERNANS

TECHNICAL FIELD

This disclosure relates to medical devices and, more particularly, to medical devices that monitor cardiac signals.

BACKGROUND

T-Wave alternans (TWA) are beat-to-beat fluctuations in amplitude, polarity, or shape of a T-wave of an electrocardiogram (ECG) or electrogram (EGM) signal, and may be used to predict sudden cardiac death (SCD). Studies have shown TWAs to have a very high negative predictive value. For example, 30% of patients indicated for an implantable cardioverter defibrillator (ICD) produce negative TWA result, and only 2-5% of these patients have a VT/VF episode. In contrast, TWA positive patients have a high likelihood of experiencing a VT/VF episode, e.g., approximately a five times higher chance compared to a negative patients.

Visible macroscopic TWA present in an ECG measured with surface electrodes have been associated with imminent onset of dangerous ventricular arrhythmias, and in some cases, may leave limited time to intervene. Microvolt level TWA can be used to assess subtle changes in repolarization that occur far in advance of arrhythmia. Microvolt level fluctuations in the T-wave are not detectable by the unaided human eye, but can be revealed with computer analysis. Measurement of surface ECG TWA requires preprocessing the input signal to reduce noise and/or analyzing 128 or more sinus beats. TWA values recorded from intracardiac EGMs of implantable cardioverter defibrillators (ICDs) and TWA recorded from surface ECGs have substantial concordance.

SUMMARY

This disclosure describes techniques for monitoring T-wave alternans (TWAs) in a patient. In particular, techniques are described for determining TWA values that make efficient use of memory. An implantable medical device (IMD), such as an implantable pacemaker, cardioverter, defibrillator, and/or monitoring device, generates an EGM signal, e.g., a far field EGM signal, and determines a TWA value based on the EGM signal.

To determine a TWA value, the IMD samples the EGM signal to obtain one or more T-wave amplitude values for each T-wave over a plurality of beats, and stores the T-wave amplitude values in memory. The IMD creates a time series of the T-wave amplitude values stored in memory, and processes the stored values in the time domain or frequency domain to determine a TWA value. As one example, the IMD may determine the TWA value based on differences between T-wave amplitude values. As an example, the IMD may calculate the power spectral density for the times series, and selects a power spectral density of a particular frequency, e.g., 0.5 beats/cycle as the TWA value.

The IMD may periodically determine TWA values for the patient and store the values in memory. The TWA values may be presented to medical personnel, e.g., as a trend. In some examples, the IMD may use the TWA value to trigger or modify therapy, or to provide an alert to the patient, a physician, a clinician, or caregiver prior to the patient experiencing a tachyarrhythmia, such as a ventricular tachycardia or ventricular fibrillation episode.

The described techniques make efficient use of memory of an IMD by storing, for each of a plurality of beats, one or more T-wave amplitude values, and in some cases a single T-wave amplitude value, in memory. In some examples, the IMD may store in memory values that are the difference between consecutive T-wave samples. In contrast, conventional TWA measurement techniques sample the ECG at a high rate throughout the T-wave in order to capture a complete morphology of the T-wave, resulting in a relatively large number of samples per beat. In some examples, the number of beats over which the EGM signal is sampled may be a programmable parameter. For example, the EGM signal may be sampled over approximately 128 beats or more.

Generally, the techniques sample the EGM signal at a predetermined interval after a fiducial point of the EGM signal. For example, the techniques may use QRS detection and a predetermined interval to sample the EGM signal over each T-wave segment for the plurality of beats. The interval may generally correspond to the time interval between the onset of the QRS complex, or some other identifiable fiducial point in the QRS complex or other component of the EGM signal, and a point of a subsequent T-wave. In some examples, the interval may correspond to time interval within a range of approximately 150 milliseconds (ms) to approximately 400 ms. Thus, the interval may be thought of as a time delay from the fiducial point, e.g., QRS complex, to the sample of the EGM signal which is selected such that the EGM signal is sampled during the subsequent T-wave.

An external computing device capable of communicating with the IMD, such as a programmer for the IMD, may operate in a configuration mode to determine the interval used by the IMD for sampling the EGM signal. The device may be configured to interface with medical leads that carry electrodes, or a device that is coupled to such leads, for receiving a 12 lead ECG signal. The external computing device determines TWA values based on the ECG signal using techniques known in the art. The device may process the ECG signal to determine TWA values for different intervals. The device may automatically upload the interval that corresponds to the largest TWA amplitude value to the IMD to be used as the interval for sampling the EGM signal.

In some examples, the IMD may determine TWA values for the patient using different intervals for different heart rates. For example, the IMD may store a reference interval in memory and automatically adjust the reference interval based on the heart of the patient. In other examples, the IMD may store in memory different intervals that correspond to different ranges of heart rates. For example, the IMD may determine TWA values using a first interval when the heart rate of the patient is approximately 60 beats per minute (bpm) to approximately 100 bpm, and may determine TWA values using a second interval when the heart of the patient is greater than 100 bpm.

In one example, a method comprises generating an electrogram (EGM) signal of a patient via one or more electrodes, storing one or more samples of the EGM signal per heart beat of the patient for a plurality of hearts beats, wherein each stored sample is an amplitude of a T-wave a predetermined interval after a fiducial point of the EGM signal, and determining a T-wave alternan (TWA) value based on the T-wave amplitudes.

In another examples, a system comprises one or more electrodes, a medical device coupled to the electrodes comprising a sensing module that senses an electrogram (EGM) signal of a patient via the electrodes, a memory, and a T-wave alternan (TWA) module that a T-wave alternan (TWA) module that stores one or more samples of the EGM signal per heart beat of the patient for a plurality of heart beats in the memory, wherein each stored sample is an amplitude of a T-wave a predetermined interval after a fiducial point of the EGM signal, and determines a T-wave alternan (TWA) value based on the stored T-wave amplitudes.

In another example, a system comprises means for generating an electrogram (EGM) signal of a patient, means for storing one or more samples of the EGM signal per heart beat of the patient for a plurality of heart beats, wherein each stored sample is an amplitude of a T-wave a predetermined interval after a fiducial point of the EGM signal, and means for determining a T-wave alternan (TWA) value based on the T-wave amplitudes.

In another example, a computer-readable storage medium comprises instructions that cause a processor to store one or more samples of an electrogram (EGM) signal of a patient per heart beat of the patient for a plurality of heart beats, wherein each stored sample of the EGM signal is an amplitude of a T-wave a predetermined interval after a fiducial point of the EGM signal, and determine a T-wave alternan (TWA) value based on the T-wave amplitudes.

The details of one or more examples are set forth in the accompanying drawings and the description below. Other features, objects, and advantages will be apparent from the description and drawings, and from the claims.

BRIEF DESCRIPTION OF DRAWINGS

FIG. 17 is a graph that illustrates example TWA values over time for a patient.

DETAILED DESCRIPTION

Figure 1:
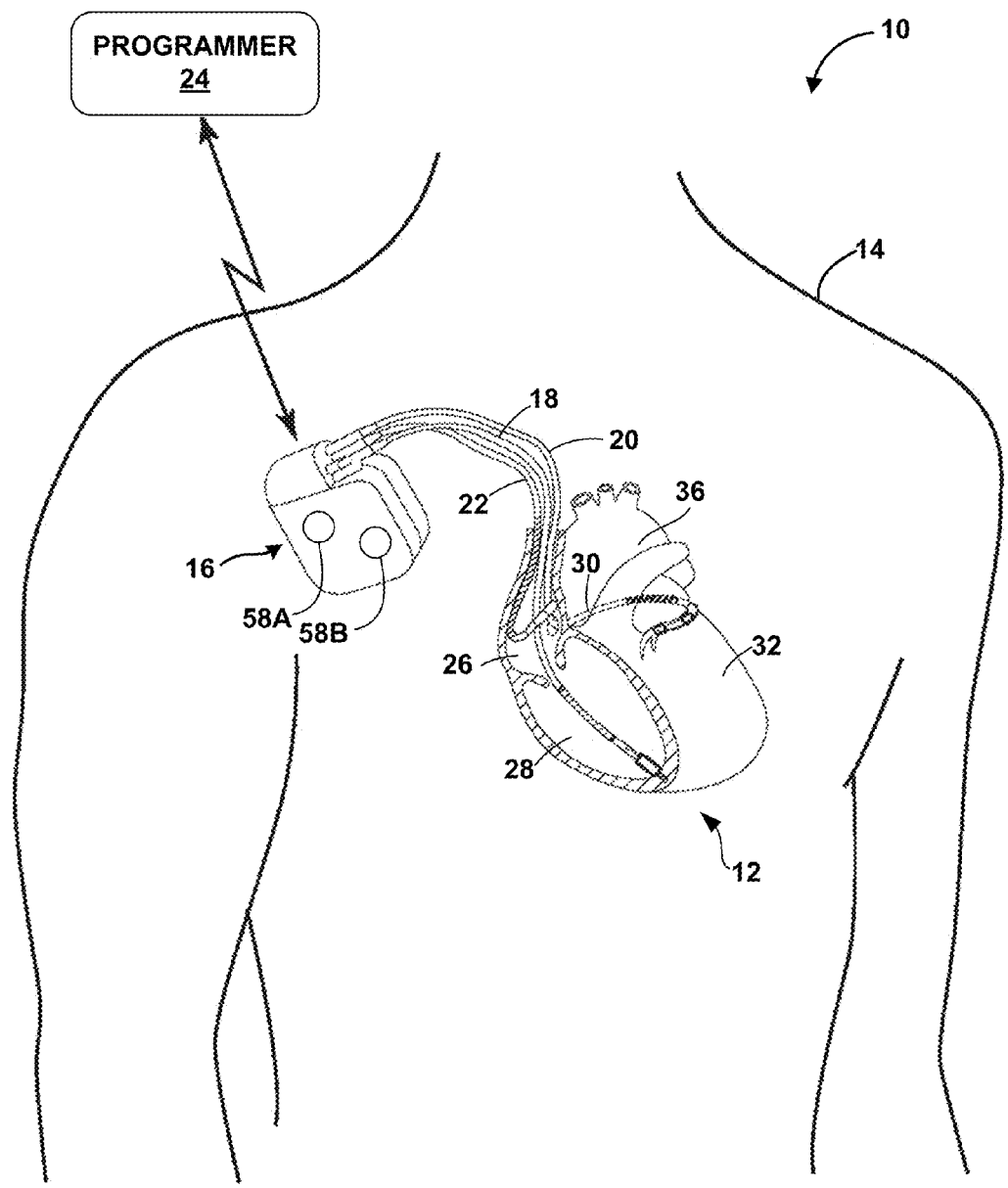
FIG. 1 is a conceptual diagram illustrating an example system for monitoring T-wave alternans (TWAs) in a patient.

FIG. 1 is a conceptual diagram illustrating an example system 10 that may be used for monitoring T-Wave alternans (TWAs) of patient 14. Generally, system 10 determines TWA values and stores the TWA values in memory. System 10 may determine TWA values periodically, such as on an hourly or daily basis, or in accordance with a predetermined or programmable schedule. System 10 may display a history of TWA values for review by a physician or other medical personnel. In some examples, system 10 generates an alarm or alert based on the TWA values. The alert may be provided to patient 14 to seek medical attention before experiencing a tachyarrhythmia, such as ventricular tachycardia (VT) or ventricular fibrillation VF, or to a physician or caregiver. System 10 may also, alternatively or additionally, provide therapy to patient 14 based on TWA values. Patient 14 ordinarily, but not necessarily, will be a human.

System 10 includes implantable medical device (IMD) 16, which is coupled to leads 18, 20, and 22, and programmer 24. In some examples, IMD 16 may be a purely diagnostic device that monitors TWAs, e.g., determines TWA values and stores the values in memory. IMD 16 may additionally provide other cardiac sensing and/or operate as a therapy delivery device to deliver electrical signals to heart 12 via one or more leads 18, 20, and 22. In some examples, IMD 16 takes the form of an implantable pacemaker, cardioverter, and/or defibrillator.

IMD 16 is not limited to devices implanted as shown in FIG. 1. As an example, IMD 16 and/or leads 18, 20 and 22 may be implanted subcutaneously or epicardially in patient 14. In other examples, the techniques described herein may be practiced by a monitoring IMD, which may not be coupled to leads, and may instead sense a cardiac electrogram (EGM) via electrodes formed on or integral with a housing of the IMD, such as housing electrodes 58A and 58B (collectively "housing electrodes 58") illustrated in FIG. 1. One example of a monitoring IMD which may be configured to practice the techniques described herein is the Reveal® monitor, which is commercially available from Medtronic, Inc., of Minneapolis, Minn. In other examples, the techniques described herein may be practiced by an external medical device with leads attached to the skin of patient 14 or implanted percutaneously in patient 14.

In operation, IMD 16 monitors an EGM signal and determines TWA values based on the EGM signal. In some examples, IMD 16 monitors a far field EGM signal. IMD 16 stores in memory one or more samples of each T-wave of the far field EGM signal for a plurality of beats. Each sample is a measurement of the amplitude of a T-wave at a particular time. A T-wave amplitude value is generally measured in microvolts (µV).

For example, IMD 16 may sample each T-wave of the EGM signal, e.g., far field EGM signal, one or more times per beat. IMD 16 generally samples the EGM signal for a plurality of beats. As an example, IMD 16 may sample the EGM signal for approximately 128 beats or more. Examples in which IMD 16 samples the EGM signal for less than 128 beats are also contemplated. Sampling the EGM signal in this way requires less data to be stored in memory of IMD 16 than techniques that store the entire T-wave morphology to compute TWA values. The number of samples of each T-wave, the number of beats over which the EGM signal is sampled, and frequency of determining TWA values may be a function of the size of the memory of IMD 16. Accordingly, these sampling parameters may be adjusted within the limitations of the memory of IMD 16.

Generally, IMD 16 samples the EGM signal at a predetermined interval after a fiducial point of the EGM signal. For example, IMD 16 may use QRS detection and one or more predetermined intervals to sample the EGM signal over each T-wave for the plurality of beats. IMD 16 may use QRS detection techniques known in the art to detect the QRS complex in the EGM signal for each beat. Each of the one or more intervals generally corresponds to a time interval between a fiducial point of the EGM and a sampling point of a subsequent T-wave. Example fiducial points of the EGM include the onset of the QRS complex, or another fiducial point of the QRS complex, e.g., the Q-wave, R-wave, S-wave or end of the QRS, or another fiducial point of the EGM. In some examples, each of the one or more intervals may be a time interval within a range of approximately 150 milliseconds (ms) to approximately 400 ms. Thus, each of the intervals may be thought of as a time delay that is triggered by the QRS complex. Upon expiration of the delay timer, IMD 16 samples the EGM signal. In some examples, rather than time, the interval is defined in terms of a number of samples subsequent to a sample of a digitized EGM associated with the fiducial point, e.g., the sample within the T-wave stored for T-wave alternans analysis as described herein is the $N^{th}$ sample subsequent the sample associated with the fiducial point.

In some examples, the interval (or intervals) may have a default value that is programmed into IMD 16 prior to operation. For example, the interval or intervals may be selected to correspond to an ascending phase, peak, or descending phase of a T-wave. However, in other examples, system 10 may operate in a configuration mode to determine one or more "optimal" intervals for patient 14. An optimal interval may be an interval that yields a relatively large TWA value. As an example, programmer 24 may operate in a configuration mode to determine one or more optimal intervals for one or more T-wave amplitude samples per beat. In the configuration mode, programmer 24 may be coupled to one or more leads attached to the skin of patient 14 (not shown), or to a device coupled to such leads, in order to receive an electrocardiogram (ECG) signal. Programmer 24 may determine TWA values for different sample points over a T-wave window, and select the interval (or intervals) based on the largest TWA value (or values).

IMD 16 processes the sampled T-wave amplitude values stored in memory to determine TWA values. IMD 16 may process the values stored in memory in a frequency domain or a time domain. To process the stored values in the frequency domain, IMD 16 may create a time series of the T-wave amplitudes, calculate the power spectral density of the time series, and select as the TWA value the power spectral density at a particular frequency, e.g., 0.5 cycles per beat. IMD 16 may calculate the power spectral density by, for example, performing a Fourier transform on the time series. IMD 16 may perform the Fourier transform by executing fast Fourier transform operations.

Alternatively, IMD 16 may process sampled T-wave amplitude values stored in memory in the time domain to determine TWA values. For example, IMD 16 may determine a difference between T-wave sampled values of consecutive T-waves, also referred to herein as T-wave pairs or pairs of T-waves, and determine the TWA value based on the differences. An example of a TWA value determined based on such differences is the mean or average of such difference.

To further increase efficient use of memory, IMD 16 may, in such examples, compute the differences on a running basis. That is, IMD 16 may temporarily store in memory samples of T-wave pairs, and permanently store in memory the difference between the sampled values. In this example, temporarily storing the samples of the T-wave pairs refers to storing the sampled T-wave values until the difference value is calculated. Once the difference value is calculated, the sampled T-wave values may be overwritten with sampled T-wave values for the subsequent pair of T-waves. IMD 16 may determine the TWA value based on difference values calculated over a plurality of T-wave pairs, such as over 64 T-wave pairs (which corresponds to 128 T-waves). Accordingly, permanently storing the difference value refers to storing the difference values for the duration of T-waves required for determining the TWA value, e.g., storing the difference values for 128 T-waves. In some examples, a TWA value may be a running average of differences, such that only the most recent N differences need to be stored to determine the current TWA value.

Generally, system 10 may compute TWA values for patient 14 periodically, e.g., in accordance with a schedule or on command. In some examples, system 10 may compute TWA values at the scheduled times without regard to the activity level or heart rate of patient 14. In such examples, system 10 may determine TWA values using a single set of one or more interval values stored in memory. Alternatively, system 10 may store multiple sets of one or more interval values in memory, where each of the sets corresponds to a different heart rate. System 10 may also store a single "reference" set of one or more interval values in memory, and automatically adjust the reference interval(s) based on the heart rate of patient 14. For example, system 10 may decrease the interval(s) for increasing heart rate and increase the interval(s) for decreasing heart rate. In other examples, system 10 may be programmed to pace heart 12 at a predetermined rate while computing TWA values. In such examples, system 10 may pace heart 12 at approximately 105 beats per minute (bpm) while computing TWA values for patient 14.

In other examples, system 10 may compute TWA values for patient 14 only when certain physiological parameters are satisfied. For example, system 10 may compute TWA values for patient 14 when the patient's heart rate exceeds a threshold value, e.g., 105 bpm, for a predetermined period of time, e.g., one minute. In general, system 10 may be capable of computing TWA values for patient 14 in accordance with a schedule, on command, or when preconditions are satisfied. Thus, in addition to storing the computed TWA values, system 10, and more particularly, IMD 16, may store physiological parameters of patient associated with the TWA values. For example, system 10 may also store the activity level, heart rate, time of day, and other information that may be useful for analyzing TWA values.

IMD 16 is configured to monitor electrical signals of heart 12. IMD 16 may monitor electrical signals of heart 12 via leads 18, 20, and 22 which extend into heart 12 of patient 14. Right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In the illustrated example, IMD 16 may sense electrical signals attendant to the depolarization and repolarization of heart 12 via electrodes coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, IMD 16 may be configured to monitor a far field EGM signal. In general, a far field EGM signal is detected via a combination of electrodes located outside of the heart. For example, one or more electrodes located on or formed integrally with a housing of IMD 16, and/or one or more electrodes located on one or more of leads 18, 20 and 22, or a different lead, may be used in combination for receiving a far field EGM.

Other configurations, i.e., number and position of leads, are possible. For example, system 10 may additionally or alternatively include temporary or permanent epicardial or subcutaneous leads, instead of or in addition to transvenous, intracardiac leads 18, 20, and 22. Such leads may be used for one or more of cardiac sensing, pacing, or cardioversion/defibrillation. Furthermore, some example configurations may not include leads coupled to an IMD, as discussed above. As another example, system 10 may include additional leads that are attachable to patient 14 when operating in a configuration mode in which a 12 lead surface ECG is used.

In some examples, programmer 24 may be a handheld computing device, computer workstation, or networked computing device. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to select values for operational parameters of IMD 16. Example programmable parameters include schedule information for determining TWA values, the interval(s) used for sampling T-wave amplitude, and other parameters associated with determining TWA values. A user may also interact with programmer 24 to retrieve physiological or diagnostic information from IMD 16.

As another example, the user may use programmer 24 to retrieve TWA values from IMD 16. That is, the user may use programmer 24 to interrogate IMD 16 to retrieve stored TWA values. The user may then view the TWA values as trends over time. The user may use the TWA trending information to guide clinical decisions. In some examples the user may use the TWA trending information to determine the presence or absence of sustained TWAs. The presence of sustained TWAs may indicate that patient 14 is at high risk of sudden cardiac death (SCD). Based on the trending information the user may, in examples in which system 10 delivers therapy to patient 14, adjust therapy parameters. In an example in which IMD 16 is monitoring device or a pacemaker, the user may modify system 10 by replacing IMD 16 with an implantable cardioverter/defibrillator.

In some examples, IMD 16 may generate an alert based on TWA values. For example, IMD 16 may identify sustained TWAs based on the computed TWA values and transmit an alert to the user via programmer 24.

In some examples, IMD 16 or programmer 24 may be configured to provide an alert based on TWA values stored in memory of IMD 16. The alert may be audible, visual, or tactile and enables patient 14 to seek medical attention to treat the condition prior to experiencing an arrhythmia, e.g., a heart failure event that may result in sudden cardiac death (SCD), such as a VT/VF episode. Alternatively the alert may enable a clinician or caregiver to direct patient 14 to seek medical attention. In some examples, the alert may be a silent alert transmitted from IMD 16 or programmer 24 to another device associated with a clinician or other user, such as a silent alert transmitted to a server, as described below, and relayed to a physician via a computing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
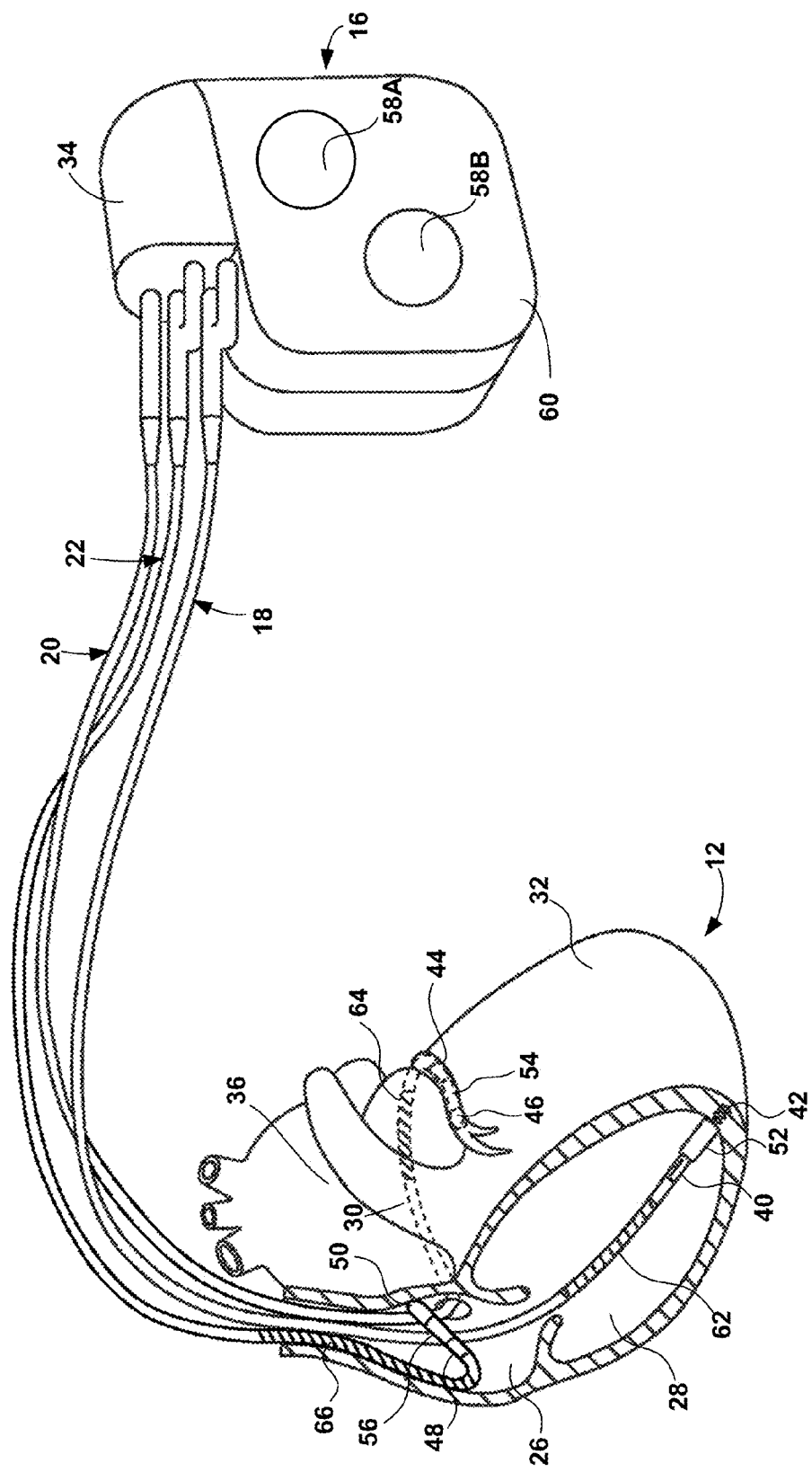
FIG. 2 is a conceptual diagram illustrating the implantable medical device (IMD) and leads of the system shown in FIG. 1 in greater detail.

FIG. 2 is a conceptual diagram illustrating IMD 16 and leads 18, 20 and 22 of therapy system 10 in greater detail. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. In some examples, coil electrode 66, or an additional coil electrode (not shown) on one of leads 18, 20 and 22, is located in the superior vena cava or otherwise outside of heart 12. In such examples, the coil electrode, or another electrode located outside of heart 12, may be used to sense electrical signals of heart 12 for a far field EGM. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2, IMD 16 includes one or more housing electrodes 58, which may be formed integrally with an outer surface of hermetically-sealed housing 60 of IMD 16 or otherwise coupled to housing 60. In some examples, housing electrodes 58 are defined by an uninsulated portion of an outward facing portion of housing 60 of IMD 16. Other division between insulated and uninsulated portions of housing 60 may be employed to define two or more housing electrodes. In some examples, a housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm and TWAs of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. In examples in which a far field EGM is monitored to measure TWA, electrodes located outside of heart, such as housing electrodes 58 or a superior vena cava coil electrode, may be used for sensing the electrical signals from heart 12. The combination of electrodes used for sensing may be referred to as a sensing configuration.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

Figure 3:
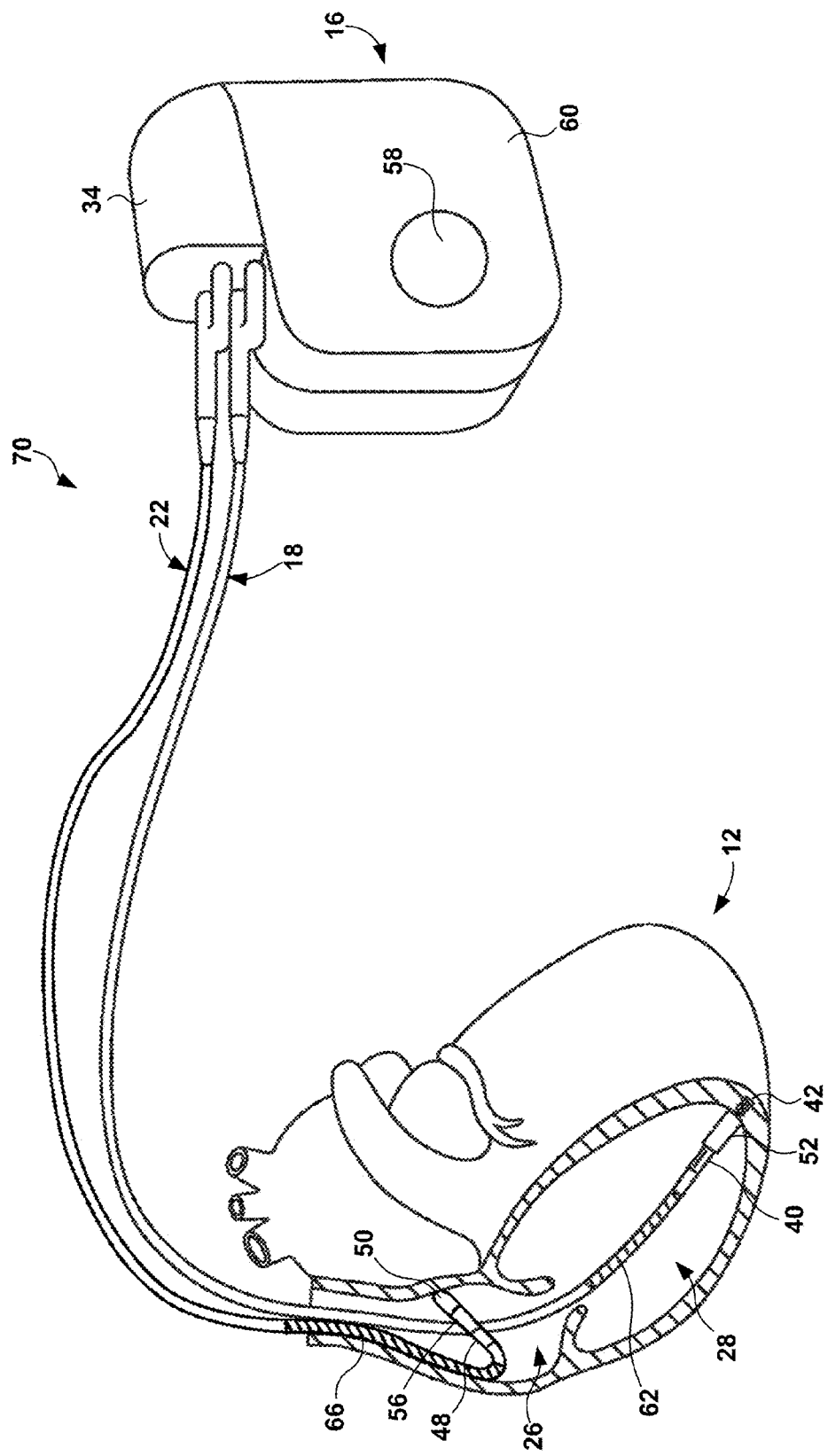
FIG. 3 is a conceptual drawing illustrating the example IMD of FIG. 1 coupled to a different configuration of implantable medical leads.

The configuration of system 10 illustrated in FIG. 2 is merely one example. In other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26. An example of this type of therapy system is shown in FIG. 3. Any electrodes located on these additional leads may be used in sensing and/or stimulation configurations.

Additionally, as previously mentioned, IMD 16 need not deliver therapy to heart 12. In general, this disclosure may be applicable to any medical device, e.g., implantable or external, that includes electrodes to sense electrical signals of heart 12 for monitoring TWAs.

FIG. 3 is a conceptual diagram illustrating another example therapy system 70, which is similar to therapy system 10 of FIGS. 1 and 2, but includes two leads 18, 22, rather than three leads. Leads 18, 22 are implanted within right ventricle 28 and right atrium 26, respectively. Therapy system 70 shown in FIG. 3 may be useful for sensing electrical signals of heart 12 as well as providing defibrillation and pacing pulses to heart 12. Monitoring TWAs according to this disclosure may be performed in two lead systems in the manner described herein with respect to three lead system. More specifically, generating EGM signals may be performed in two lead systems in the manner described herein with respect to three lead systems.

Figure 4:
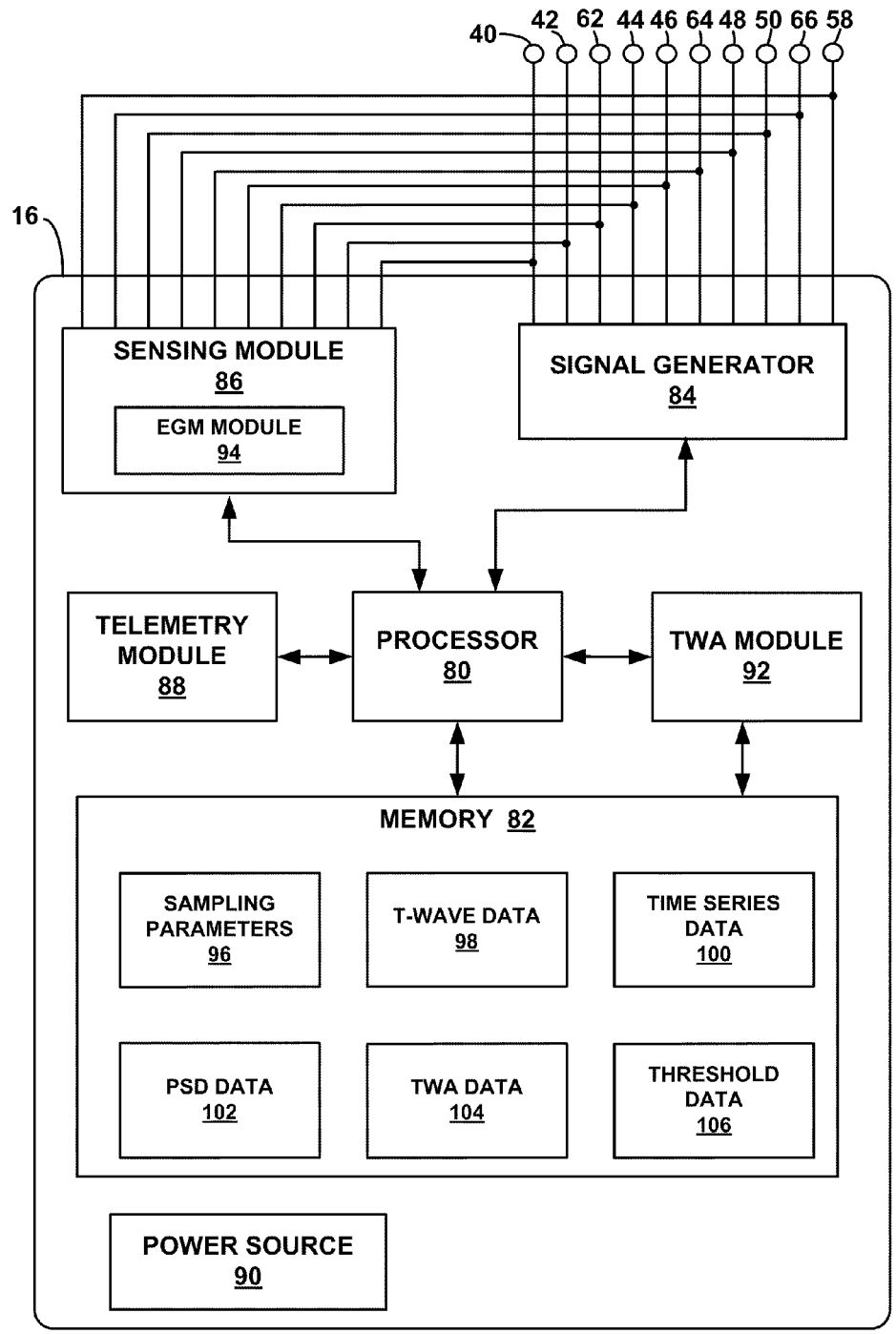
FIG. 4 is a block diagram illustrating an example configuration of the IMD.

FIG. 4 is a block diagram illustrating one example of IMD 16 which includes processor 80, memory 82, stimulation generator 84, sensing module 86, telemetry module 88, power source 90, and TWA module 92. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

In examples in which IMD delivers electrical stimulation therapy, processor 80 controls signal generator 84 to deliver stimulation therapy to heart 12 according to a selected one or more of therapy programs, which may be stored in memory 82. Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver stimulation pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12. Sensing module 86 may also include a switch module (not shown) to select which of the available electrodes are used to sense the heart activity, depending upon which electrode combination is used in the current sensing configuration. In some examples, processor 80 may select the electrodes that function as sense electrodes, i.e., select the sensing configuration, via the switch module within sensing module 86.

Sensing module 86 may include one or more detection channels, each of which may comprise an amplifier. The detection channels may be used to sense the cardiac signals. Some detection channels may detect events, such as R- or P-waves, and provide indications of the occurrences of such events to processor 80 in accordance with techniques well known in the art. One or more other detection channels may be part of an EGM module 94. Such channels may provide the signals to an analog-to-digital converter of the EGM module 94. EGM module 94 may provide the digital EGM to processor 80 or TWA module 92 for processing or analysis by processor 80 or TWA module 92.

For example, sensing module 86 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 80 or TWA module 92 then uses that detection in measuring frequencies of the sensed events. Different narrow band channels of sensing module 86 may have distinct functions. For example, some various narrow band channels may be used to sense either atrial or ventricular events. With respect to the techniques described in this disclosure, TWA module 92 may sense atrial or ventricular events to detect a QRS complex and/or determine a heart rate of patient 14.

In one example, at least one narrow band channel may include an R-wave amplifier that receives signals from the sensing configuration of electrodes 40 and 42, which are used for sensing and/or pacing in right ventricle 28 of heart 12. Another narrow band channel may include another R-wave amplifier that receives signals from the sensing configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In the illustrated example, sensing module 86 includes EGM module 94. EGM module 94 may include a wide band channel which may comprise an amplifier with a relatively wider pass band than the R-wave or P-wave amplifiers. Signals from the selected sensing electrodes that are selected for coupling to this wide-band amplifier may be converted to multi-bit digital signals by an analog-to-digital converter (ADC) provided by EGM module 94. Processor 80 or TWA module 92 may employ digital signal analysis techniques to characterize the digitized signals from the wide band channel to, for example detect and classify the patient's heart rhythm. Processor 80 may detect and classify the patient's heart rhythm by employing any of the numerous signal processing methodologies known in the art. In some examples, TWA module 92 may analyze the EGM signal to detect within the EGM signal a QRS complex or other fiducial point of the EGM signal for each of a plurality of beats and sample the EGM signal at one or more predetermined intervals with reference to the detected fiducial point.

Processor 80 may maintain programmable counters associated with time intervals. For example, if IMD 16 is configured to generate and deliver pacing pulses to heart 12, processor 80 may maintain programmable counters which control the basic time intervals associated with various modes of pacing, including pacing for cardiac resynchronization therapy (CRT) and anti-tachycardia pacing (ATP). Intervals defined by processor 80 may include atrial and ventricular pacing escape intervals, refractory periods during which sensed P-waves and R-waves are ineffective to restart timing of the escape intervals, and the pulse widths of the pacing pulses. The durations of these intervals may be determined by processor 80 in response to stored data in memory 82. Processor 80 may also determine the amplitude of the cardiac pacing pulses.

Processor 80 may reset interval counters upon sensing of R-waves and P-waves with detection channels of sensing module 86. The value of the count present in the interval counters when reset by sensed R-waves and P-waves may be used by processor 80 to measure the durations of R-R intervals, P-P intervals, PR intervals and R-P intervals, which are measurements that may be stored in memory 82. Processor 80 may use the count in the interval counters to detect a suspected tachyarrhythmia event, such as ventricular fibrillation or ventricular tachycardia. A portion of memory 82 may be configured as a plurality of recirculating buffers, capable of holding series of measured intervals, which may be analyzed by processor 80 to determine whether the patient's heart 12 is presently exhibiting atrial or ventricular tachyarrhythmia. In embodiments in which IMD 16 is configured for pacing, processor 80 may also reset the interval counters upon the generation of pacing pulses by signal generator 84, and thereby control the basic timing of cardiac pacing functions, including anti-tachyarrhythmia pacing.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 220 milliseconds (ms) and fibrillation when the interval length falls below 180 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

TWA module 92 determines TWA values for patient 14 based on EGM signals received from EGM module 94. To determine TWA values, TWA module 92 retrieves from memory 82 sampling parameters 96. Example sampling parameters include parameters that specify the one or more sampling intervals, the number of samples per beat, the number of beats over which to the sample the EGM signal for determining a TWA value, and the frequency for determining TWA values. Additional example sampling parameters include parameters that specify whether to determine TWA values while pacing the heart of patient 14 and the pacing rate. Yet additional example sampling parameters include parameters that specify physiological conditions to be met for determining TWA values, such as a minimum heart rate and a duration for the minimum heart rate. Each of sampling parameters 96 may have a default value, but may also be manually adjusted by a user using programmer 24.

TWA module 92 samples the EGM signals received from EGM module 94 in accordance with sampling parameters 96 and stores the sampled data as T-wave data 98. As previously described, TWA module 92 samples each T-wave the EGM signal over a plurality of consecutive beats. Accordingly, T-wave data 98 stores a plurality of T-wave amplitude values. The number of T-wave amplitude values stored as T-wave data 98 corresponds to the number of beats over which TWA module 92 samples the EGM signal and the number of samples obtained for each T-wave.

TWA module 92 generates time series data 100 from T-wave data 98. For example, TWA module 92 may create time series data 100 as a time ordered sequence of T-wave data 98. In the illustrated example, TWA module 92 processes T-wave data 98 in the frequency domain to determine a TWA value. Thus, TWA module 92 generates power spectral density (PSD) data 102 from time series data 100. For example, TWA module 92 may perform a Fourier transform operation on time series data 100, such as a fast Fourier transform (FFT), to generate PSD values for the time series. TWA module 92 selects a value from PSD data 102 to store as TWA data 104.

In other examples, TWA module 92 may process T-wave data 98 in the time domain to determine a TWA value. In such examples, TWA module 92 may store values that are the difference between T-wave pairs or other values that can be used for determining the variance of T-waves and, for example, determine a mean or average of such differences as the TWA value Generally, TWA module 92 periodically determines TWA values in accordance with a schedule. In some examples, TWA module 92 determines TWA values when patient 14 satisfies one or more physiological conditions. In any case, for each time period that TWA module 92 determines a TWA value, the values stored in T-wave data 98, time series 100, and PSD data 1092 may be overwritten. That is, TWA module 92 stores value for only the current time period in each of T-wave data 98, time series data 100, and PSD data 102. TWA data 104, however, stores the TWA value determined for each time period. Accordingly, the TWA values stored in TWA data 104 may be transmitted to programmer 24 or another external device to prevent loss of information. IMD 16 may transmit TWA values to programmer 24 in accordance with a schedule or upon interrogation by programmer 24.

In some examples, TWA module 92 may generate an alert based on a comparison of TWA data 104 to threshold data 106. Threshold data 106 may store a threshold value that, when exceeded by one or more of TWA data 104, indicates a high likelihood that patient 14 will experience a tachyarrhythmia, such as a VT/VF episode. The threshold may be a predetermined value, which may be selected by a user, a baseline value determined for the patient based on a baseline TWA measurement, e.g., at the time of implantation of IMD 16, or a value determined based on a average of previous TWA measurements, which may be modified as new TWA measurements are made.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna (not shown), which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374, 382 to Markowitz, entitled, "MARKER CHANNEL TELEMETRY SYSTEM FOR A MEDICAL DEVICE," which issued on Feb. 15, 1983 and is incorporated herein by reference in its entirety.

In addition, processor 80 may transmit TWA related information to programmer 24 or another external computing device via telemetry module 88. For example, processor 80 may send one or more values stored as TWA data 104 to programmer 24 or another external computing device via telemetry module 88. That is, IMD 16 may transmit the processed data (TWA values) to programmer 24 or another external computing device for reporting purposes, e.g., for providing an alert to patient 12 or another user, or so that the external device may present the received TWA values to a physician for analysis. As an example, programmer 24 or another external computing device may display the received TWA values as a trend diagram or histogram that may be used by the physician for making TWA related medical decisions. In some examples, TWA module 92 may generate the trend diagram or histogram, or determine whether to provide an alert. In other examples, programmer 24 or another external computing device may generate the trend diagram or histogram, or determine whether to provide an alert, based on TWA data received from IMD 16 via telemetry module 88.

TWA module 92 may also receive TWA related information from programmer 24 or another computing device via telemetry module 88. For example, TWA module 92 may receive information for programming one or more of sampling parameters 96, i.e., selecting a value for one or more of sampling parameters 96, via telemetry module 88. In some examples, IMD 16 may communicate with a network such as the Medtronic CareLink® Network developed by Medtronic, Inc., of Minneapolis, Minn., or some other network linking patient 14 to a clinician. In such examples, IMD 16 may pass TWA data 104, an alert, a trend diagram, or a histogram to, or receive sampling parameters from, a computing device via the network.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis.

Although illustrated separately in the example of FIG. 4, TWA module 92 may be incorporated in a single processing unit with processor 80, or may be a functional module executed or provided by processor 110. In other examples, TWA module 92 may be provided via a separate hardware component from processor 80, or by a separate device from IMD 16. The functions attributed to processor 80 and TWA module herein may be embodied as software, firmware, hardware or any combination thereof.

Figure 5:
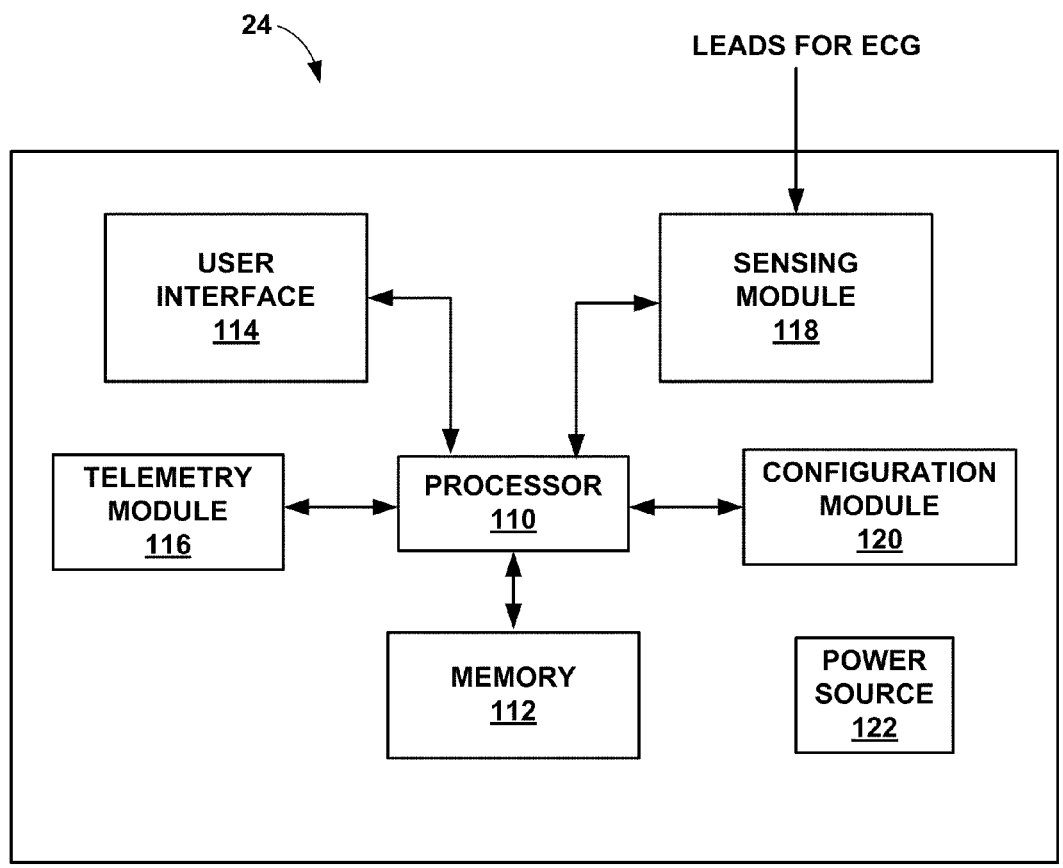
FIG. 5 is a block diagram illustrating an example configuration of the programmer shown in FIG. 1.

FIG. 5 is functional block diagram illustrating an example configuration of programmer 24. As shown in FIG. 5, programmer 24 may include a processor 110, memory 112, user interface 114, telemetry module 116, sensing module 118, configuration module 120, and power source 122. Programmer 24 may be a dedicated hardware device with dedicated software for interacting with IMD 16. Alternatively, programmer 24 may be an off-the-shelf computing device running an application that enables programmer 24 to interact with IMD 16.

Generally, a clinician, physician, medical technician, or other authorized user may interact with programmer 24 via user interface 114, which may include a display to present a graphical user interface to a user, and a keypad or other mechanism for receiving input from a user. A user may use programmer 24 to select values for the operational parameters of IMD 16 (FIG. 1).

With respect to the techniques described in this disclosure, a user may use programmer 24 to select values for sampling parameters 96, or to view a history of TWA values 104. A user may view a history of TWA values as a histogram or other graphical representation. In such examples, the user, e.g., a clinician, may view the history of TWA values to guide clinical decisions. A clinician may select new therapies or therapy parameters, or modify therapy parameters, based on the history of TWA values. In an example in which IMD 16 is a purely diagnostic or monitoring device, a clinician may decide to replace IMD 16 with an IMD capable of delivering pacing and/or cardioversion/defibrillation to the patient based on the history of TWA values.

In some examples, programmer 24 may provide an alert to a user of programmer 24. Alerts provided via user interface 114 may include a silent, audible, visual, or tactile alert. For example, user interface 114 may emit a beeping sound, display a text prompt, cause various buttons or screens to flash, or vibrate to alert patient 14, a physician, or another user that TWA values have exceeded a threshold. Patient 14 may then seek medical attention, e.g., check in to a hospital or clinic, to receive appropriate treatment, or the other user may instruct patient 14 to do so.

In some examples, programmer 24 may also be used to determine an optimal sampling interval or intervals that may be used by IMD 16 on a beat-to-beat basis to determine TWA values. When operating programmer 24 in a configuration mode, programmer 24 may be configured to receive an ECG. In the illustrated example, programmer 24 includes a sensing module 118 coupled to one or more medical leads attached to the skin of patient 14. Sensing module 116 may operate similar to sensing module 86 to generate digitized ECG signal, based on the electrical signals received from the sensing electrodes of the attached medical leads. In some examples, programmer 24 may be configured to generate a 12 lead ECG signal. In other examples, processor 110 or configuration module 120 of programmer 24 may receive a digitized ECG signal from another device coupled to the patient by external leads.

Configuration module 120 processes the ECG signal for a plurality of beats to determine one or more TWA values. Configuration module 120 determines each of the TWA values using a different sampling interval over the plurality of beats. The complete morphology of the T-waves over the plurality of beats may be stored in memory 112.

Configuration module 120 may select as the optimal sampling interval, the sampling interval that corresponds to the largest TWA value determined over the plurality of beats. In examples in which IMD 16 will record a plurality of T-wave amplitudes for each of a plurality of beats for the TWA analysis, configuration mode may select a plurality of intervals for chronic, ambulatory use based on their TWA during the configuration mode. Each sampling interval may be thought of as corresponding to a specific time within a T-wave window. The T-wave window may be defined as the interval over which a T-wave is expected following a QRS complex or other fiducial point of the EGM signal. Thus, each sampling interval corresponds to a different sampling point over the T-wave window.

In some examples, configuration module 120 may determine an optimal sampling interval for different heart rates. In such examples, programmer 24 may be configured to also deliver pacing pulses to patient 14, an external device separate from programmer 24 may be used to deliver the pacing pulses, or programmer 24 may control IMD 16 to deliver the pacing pulses. In any case, configuration module 120 may determine one or more TWA values over a plurality of beats for each of the different heart rates. Programmer 24 transmits the one or more optimal sampling intervals to IMD 16 via telemetry module 116.

The one or more sampling intervals selected by configuration module 120 are used to determine the delay timer value that will be used by IMD 16 to determine when, relative to a detected QRS complex, e.g., the beginning or R-wave of the QRS complex, the T-wave amplitude should sampled for the cardiac beat comprising the QRS complex. Programmer 24 may automatically upload this optimal delay timer value to IMD 16 via telemetry module 116. A more detailed description for determining the optimal sampling interval or optimal delay timer is provided in FIG. 11.

Processor 110 can take the form one or more microprocessors, DSPs, ASICs, FPGAs, programmable logic circuitry, or the like, and the functions attributed to processor 110 herein may be embodied as hardware, firmware, software or any combination thereof. Configuration module 120, although illustrated as a separate module in FIG. 5, may be incorporated in a single processing unit with processor 110, or may be a functional module executed or provided by processor 110.

Memory 112 may store instructions that cause processor 110 to provide the functionality ascribed to programmer 24 herein, and information used by processor 110 to provide the functionality ascribed to programmer 24 herein. Memory 112 may include any fixed or removable magnetic, optical, or electrical media, such as RAM, ROM, CD-ROM, hard or floppy magnetic disks, EEPROM, or the like. Memory 112 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 116, which may be coupled to an internal antenna or an external antenna. An external antenna that is coupled to programmer 24 may correspond to the programming head that may be placed over heart 12, as described above with reference to FIG. 1. Telemetry module 116 may be similar to telemetry module 88 of IMD 16 (FIG. 4).

Telemetry module 116 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device, such as a server capable of processing information retrieved from IMD 16.

In some examples, processor 110 of programmer 24 and/or one or more processors of one or more networked computers may perform all or a portion of the techniques described herein with respect to processor 80 and IMD 16. For example, processor 110 or another processor may implement a TWA module 92 and/or determine TWA values for a patient based on T-wave data 98 received from IMD 16.

Figure 6:
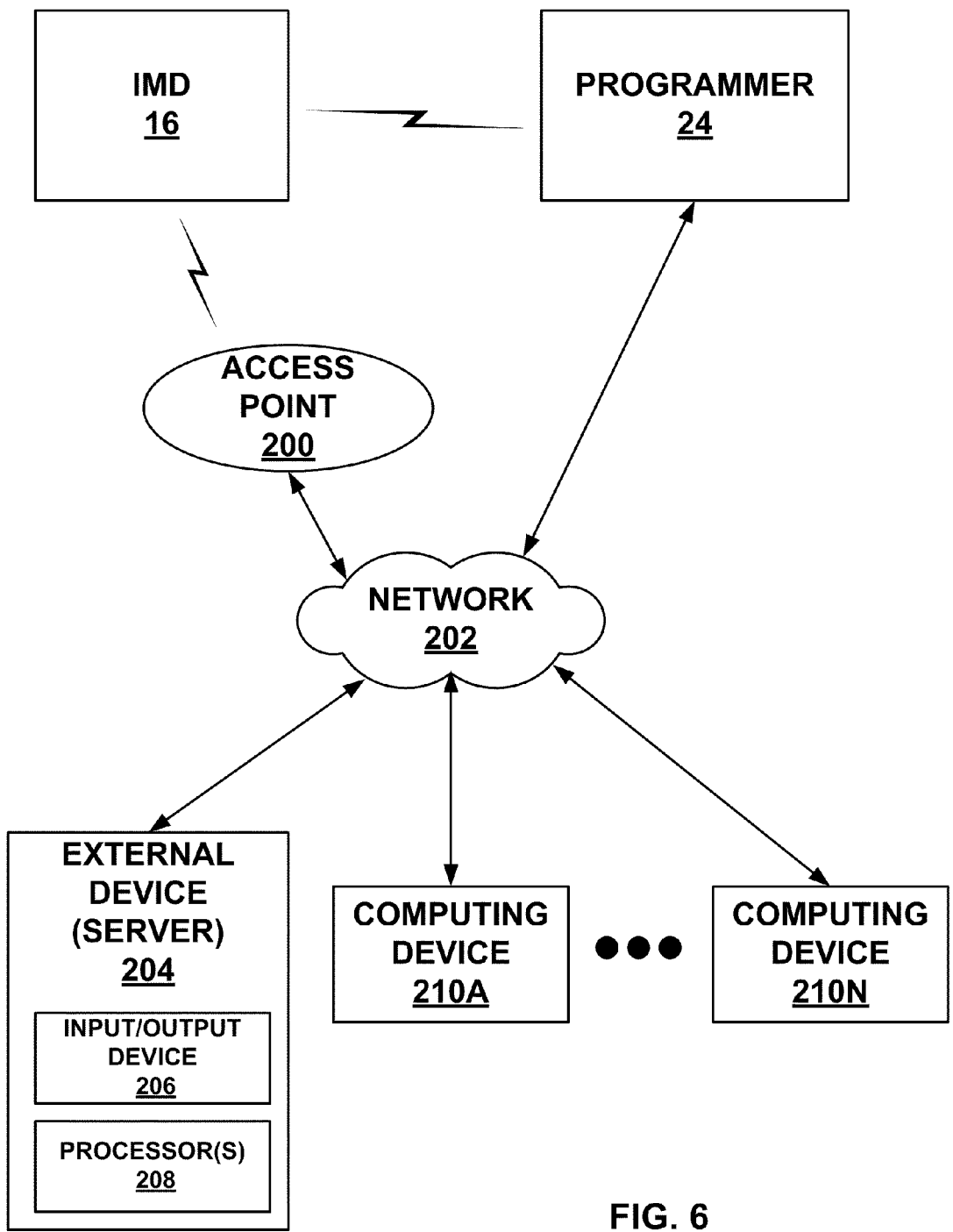
FIG. 6 is a block diagram illustrating an example system that includes an external device, such as a server, and one or more computing devices that are coupled to the IMD and programmer shown in FIG. 1 via a network.

FIG. 6 is a block diagram illustrating an example system that includes an external device, such as a server 204 including an input/output device 206 and processor(s) 208, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communicate with an access point 200 via a second wireless connection. In the example of FIG. 6, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, access point 200, server 204, and computing devices 210A-210N may each comprise one or more processors 208, such as one or more microprocessors, DSPs, ASICs, FPGAs, programmable logic circuitry, or the like, that may perform various functions and operations, such as those described herein.

Access point 200 may comprise a device that connects to network 202 via any of a variety of connections, such as telephone dial-up, digital subscriber line (DSL), or cable modem connections. In other embodiments, access point 200 may be coupled to network 202 through different forms of connections, including wired or wireless connections. In some embodiments, access point 200 may be co-located with patient 14, and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. Network 202 may comprise a local area network, wide area network, or global network, such as the Internet.

In some embodiments, access point 200, server 204, or computing devices 210 may control or perform any of the various functions or operations described herein, such as the functionality associated with determining TWA data 102. In some examples, one or more of access point 200, server 204, or computing devices 210 may include a TWA module 92 and/or provide at least some of the functionality ascribed herein to TWA module 92 or IMD 16. For example one or more of these external devices may receive T-wave data 98 from IMD 16, and determine TWA data 104 using the techniques described herein. One or more of access point 200, server 204, or computing devices 210 may compare TWA data 104 to threshold data 106, and may generate an alert based on the comparison. One or more of access point 200, server 204, or computing devices 210 may generate a trend diagram or otherwise format TWA data 104 for presentation to a user, and present such data to the user.

In some examples, server 204 communicates with IMD 16 or programmer 24, and retrieves TWA data 104 or alerts from the IMD or programmer. Server 204 may be configured to provide a secure storage site for archival of TWA data that has been collected from IMD 16 and/or programmer 24. In some cases, programmer 24 or server 204 may assemble TWA data in web pages or other documents for viewing by and trained professionals, such as clinicians, via viewing terminals associated with computing devices 210. Server 204 may also relay alerts to computing devices 210, e.g., in the form of web pages, emails, or other messaging or communication techniques. The system of FIG. 6 may be implemented, in some aspects, with general network technology and functionality similar to that provided by the Medtronic CareLink® Network developed by Medtronic, Inc., of Minneapolis, Minn.

Figure 7:
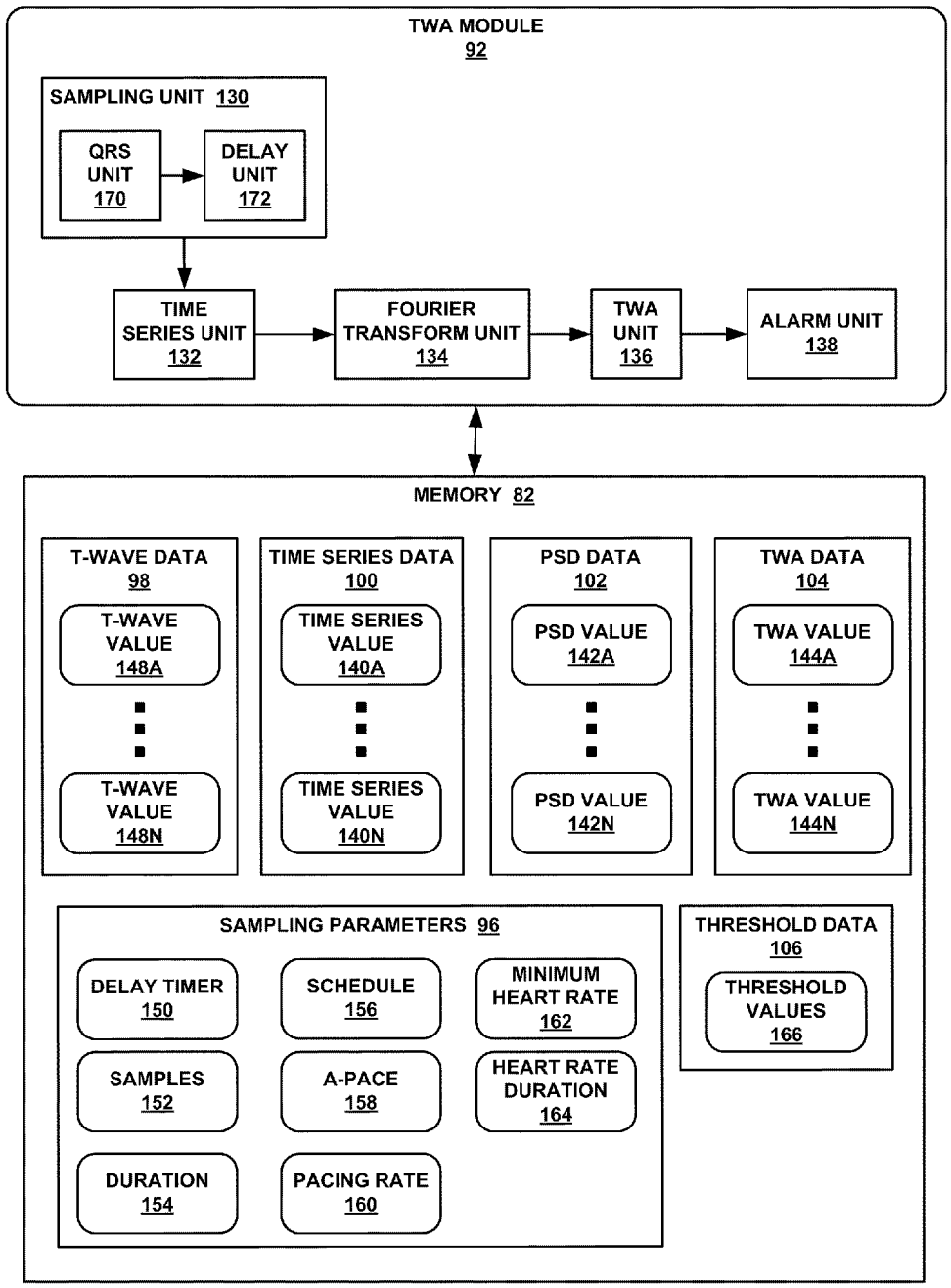
FIG. 7 is a block diagram illustrating the memory of the IMD shown in FIG. 4 in greater detail and an example configuration of a TWA module.

FIG. 7 is a block diagram illustrating an example configuration of TWA module 92 in conjunction with memory 82 of IMD 16. As shown in FIG. 7, TWA module 92 includes multiple components including sampling unit 130, time series unit 132, Fourier transform unit 134, TWA unit 136, and alarm unit 138. Units 130, 132, 134, 136, and 138 (and their sub-units described below with reference to FIG. 7) may be implemented in one or more processors or devices described herein, such as processor 80 of IMD 16. The units of TWA module 92 (and their sub-units) may be embodied as one or more hardware modules, software modules, firmware modules, or any combination thereof. As illustrated in FIG. 7, the units and sub-units of TWA module 92 may have access to memory 82 for buffering or storing any of the values discussed with reference to FIG. 7, e.g., at locations accessible by and known to these units.

Generally, TWA module 92 determines TWA values based on EGM signals received from sensing module 86 of IMD 16 in accordance with the techniques described in this disclosure. TWA module 92 retrieves from memory 82 parameters required to execute the described sampling method, i.e., sampling parameters 96, from memory 82. TWA module 92 also stores data for determining TWA values, and the TWA values themselves within memory 82.

Sampling unit 130 samples EGM signals received from sensing module 86 in accordance with the techniques described in this disclosure. In the illustrated example, sampling unit 130 includes QRS unit 170 and delay unit 172. QRS unit 170 and delay unit 172 operate in a coordinated manner to sample the received EGM signals and store the sampled values as T-wave data 98 within memory 82. As previously described, each of the sampled EGM signal values may be a T-wave amplitude value. Accordingly, T-wave data 98 is shown in FIG. 7 as including T-wave values 148A-N. Each of T-wave values 148A-N is a different T-wave amplitude value. In an example in which sampling unit 130 samples the received EGM signal one time for each of 128 consecutive beats, T-wave values 148A-N represent the 128 sampled T-wave amplitude values. As discussed above, sampling unit 130 may sample the received EGM signal more than one time per beat, in some examples. The operation of QRS unit 170 and delay unit 172 are described in greater detail below.

Sampling unit 130 may, in some examples, sample the received EGM signals over multiple time periods. The multiple time periods may be periodic or provided by a predetermined or programmable schedule. In such examples, sampling unit 130 retrieves schedule 156 from sampling parameters 96 stored in memory 82. Schedule 156 may provide periodic intervals for sampling EGM signals received from sensing module 86. The periodic intervals determine the start time and frequency for sampling the received EGM signals. For example, schedule information 156 may provide hourly intervals, daily intervals, or weekly intervals. An authorized user may manually program the intervals for schedule 156 via programmer 24.

In some examples, sampling unit 130 samples the received EGM signals while IMD 16, programmer 24, or another device external to the patient paces the heart of the patient. In the illustrated example, IMD 16 selectively delivers pacing pulses to the heart of the patient while determining TWA values based on two pacing parameters, i.e., A-pace 58 and pacing rate 160, which sampling unit 130 retrieves from sampling parameters 96. A-pace 158 may store a Boolean value that controls whether pacing pulses are delivered to the patient while IMD 16 determines TWA values. For example, sampling unit 130 may send a control signal to invoke signal generator 84 when A-pace 158 stores a TRUE value. Stimulation generator 84 paces the heart of the patient at the rate specified by pacing rate 160 when A-pace 158 is TRUE. An example pacing rate may be approximately 105 beats per minute (bpm).

When A-pace 158 stores a FALSE value, sampling unit 130 may sample the received EGM signal according to schedule 156 and without regard to the heart rate of the patient. In an example in which IMD 16 does not pace the heart of the patient, sampling unit 130 may use different sampling intervals to sample the received EGM signal based on the heart rate of the patient. Delay timer 150 may store a plurality of sampling intervals that each corresponds to a different heart rate. For example, delay timer 150 may store a first sampling interval that corresponds to a heart rate of approximately 40 bpm to approximately 100 bpm, and a second sampling interval that corresponds to a heart rate greater than approximately 100 bpm. In such an example, processor 80 may determine the heart rate of the patient, for example by counting R-R intervals over a period of time. Sampling unit 130 retrieves the appropriate sampling interval stored within delay timer 150 and samples the received EGM signal in accordance with the selected sampling interval.

In some examples, sampling unit 130 may automatically adjust delay timer 150 based on the heart rate of the patient. For example, the interval of the T-wave and temporal relationship relative to the QRS complex may change as a function of heart rate. In such examples, delay timer 150 may automatically adjust timer delay 150 based on the heart rate. Delay timer 150 may store a reference value that corresponds to a known heart rate and delay unit 172 may adjust the reference value based on the function, and use the adjusted value for sampling the received EGM signal.

In other examples, sampling unit 130 may not sample received EGM signals in accordance with schedule 156. Instead, sampling unit 130 may sample received EGM signals when certain preconditions are satisfied. In the example illustrated in FIG. 7, sampling unit 130 may sample received EGM signals based on minimum heart rate 162 and heart rate duration 164 retrieved from sampling parameters 96 stored in memory 82. Sampling unit 130 samples the received EGM signals when the patient's heart rate is greater than minimum heart rate 162 for an interval greater than heart rate duration 164. An example value for minimum heart rate 162 is approximately 105 bpm. An example value for heart rate duration 164 is approximately one minute.

In any case, sampling unit 130 initiates the described techniques for determining TWA values based on one or more of schedule 156, A-pace 158, pacing rate 160, heart rate threshold 162, and heart rate duration 164. For example, sampling unit 130 initiates the described method by applying EGM signals generated by sensing module 86 to QRS unit 170 and delay unit 172. Under the control of sampling unit 130, QRS unit 170 processes the EGM signal to detect a QRS complex for each of the plurality of beats. QRS unit 170 may employ various digital or analog signal processing techniques known in the art for detecting the QRS complex within an EGM signal. For example, QRS unit 170 may detect the onset of the QRS complex, the R-wave, or any other identifiable fiducial point of the QRS complex.

QRS unit 170 activates delay unit 172 after detecting a QRS complex within the EGM signal. In some examples, QRS unit 170 may also provide data related to the QRS complex (timing data) to delay unit 172. For example, QRS unit 170 may provide data to delay unit 172 that marks the time of detection of QRS complex.

Delay unit 172 controls the timing of the sampling of the EGM signal by sampling unit 130 based on delay timer 150 and any data that may be received from QRS unit 170. Delay timer 150 may store a value that corresponds to an interval of time between the detection of the QRS complex and a point for sampling the subsequent T-wave. An example T-wave may appear over an interval approximately 150 ms to 400 ms following the detection of the QRS complex. This 250 ms interval may be thought of as a T-wave window where the sampling interval is defined as the interval between the detection of the QRS complex and a point within the T-wave window at which the EGM signal is sampled. Thus, delay timer 150 may store a value within a range of approximately 150 ms to approximately 400 ms.

Because of the relationship between the time interval and the discrete values that comprise the EGM signal, delay timer 150 may alternatively store an integer value that specifies the number of the data points from the detection of the QRS complex to the data point for the EGM signal that corresponds to the appropriate sample time. As an example, if the EGM signal is generated at 256 Hz and a T-wave window is selected to be approximately 250 ms, then delay timer 150 may store an integer within the range of approximately 38 to approximately 102 because the T-wave following the detected QRS complex is expected to be represented by the $38^{th}$-$102^{nd}$ data points following the detected QRS complex. In some examples, the T-wave window may be approximately 120 ms. In examples in which sampling unit 130 samples the EGM signal a plurality of time per beat, delay timer 150 may store a plurality of values, each of the values associated with a different one of the samples per beat.

Sampling unit 130 samples the EGM signal in this way for a plurality of heart beats. Duration 154 is a sampling parameter 96 specifies the number of heart beats over which sampling unit 130 may sample the received EGM signal. For example, sampling unit 130 may sample the EGM signal over 128 or more consecutive heart beats. In other examples, sampling unit 130 may sample the received EGM signal for fewer than 128 consecutive beats, e.g., 64 consecutive heart beats.

In some examples, sampling unit 130 obtains more than one samples of each T-wave of the EGM signal for the specified number of beats. In such examples, sampling unit 130 retrieves samples parameter 152 from sampling parameters 96 stored in memory 82. Samples parameter 152 specifies the number of samples that sampling unit 130 obtains for each T-wave of the received EGM signal. As an example, samples parameter 152 may be an integer value selected within a range of approximately one to fifty, or approximately one to ten. Sample parameter 152 may be a value equal to five, four, three, or two, as examples. Values larger than ten or fifty may be used, but the upper limit of samples parameter 152 is dependent on the limitations of memory 82.

It should be understood that more than one sample per T-wave may be obtained, but the number of samples per T-wave is generally in accordance with the size of the memory of IMD 16. In examples in which each T-wave is sampled more than once, various algorithms are contemplated for determining one or more corresponding TWA values. As one example, TWA values may be computed for each of the different sampling intervals. Each of the different TWA values may be displayed via programmer 24 or a "final" TWA value may be determined from the different TWA values. The final TWA value, for example, may be an average of the different TWA values or the final TWA value may be selected as the largest of the different TWA values.

It should be understood that there exists a relationship between samples parameter 152 and delay timer 150, which specifies the time delay between the QRS complex and the sampling point. That is, in examples in which sampling unit 130 obtains more than one sample of each T-wave of the received EGM signals, the time at which each sampled is obtained should also be specified. Accordingly, design choices may be made regarding the handling of sampling parameters for the described sampling techniques.

As one example, delay timer 150 may store a plurality of values that each correspond to a different sampling interval. As an example, three sampling intervals may be used in which a first sampling interval corresponds to an ascending phase of a T-wave, a second sampling interval corresponds to a peak of the T-wave, and a third sampling interval corresponds to a descending phase of the T-wave. In such an example, delay timer 150 may store first, second, and third values that corresponds to the first, second, and third sampling intervals.

As another example, sampling unit 130 may utilize a method for sampling each T-wave around delay timer 150. That is, if sampling unit 130 obtains two samples per T-wave, sampling unit 130 may sample each T-wave at an equal time before and after the value of delay timer 150. If sampling unit 130 obtains three samples per T-wave, sampling unit 130 may sample each T-wave at the value of delay timer 150 and at equal times before and after delay timer 150.

As yet another example, sampling unit 130 may sample the EGM signal at the value specified by delay timer 150 and at subsequent equally spaced intervals. The number of intervals may be specified by samples 152. Example intervals may be approximately 2 ms intervals, 5 ms intervals, or the like.

Sampling unit 130 activates time series unit 132 when sampling of the EGM signal is complete, i.e., when the T-wave amplitude values are stored in memory 82. Time series unit 132 retrieves T-wave values 148A-N and arranges the values in a time ordered sequence. Time series unit 132 stores the time ordered sequence in memory 82 as time series data 100. In the illustrated example, time series data 100 include time series values 140A-N. Generally, the number of time series values 140A-N is equal to the number of T-wave amplitude values 148A-N. Time series unit 132 activates Fourier transform unit 134 after generating time series data 100.

Fourier transform unit 134 processes time series data 100 to determine power spectral density (PSD) data 102. For example, Fourier transform unit 134 may perform fast Fourier transform (FFT) operations on time series data 100 or employ other discrete Fourier transform (DFT) techniques to generate PSD data 102. In the illustrated example, PSD 102 includes PSD values 142A-N. The number of PSD values 142A-N may be dependent on the Fourier transform method used to operate on time series data 100. Fourier transform unit 134 activates TWA unit 136 after storing frequency values 142A-N in memory 82.

TWA unit 136 select one of PSD values 142A-N to store as TWA data 104. For example TWA unit 136 may select the one of PSD values 142A-N for a particular frequency. In some examples, TWA unit 136 may the PSD value for 0.5 cycles per beat. In some examples, TWA unit 136 may also store associated information as TWA data 104. For example, when TWA module 92 TWA unit 134 may also store the heart rate of the patient and date information as TWA data 104. Accordingly, TWA data 104 includes TWA values 104A-N where each of the values corresponds to a TWA value determined at a different time.

Alarm unit 138 is invoked by TWA unit 136, for example, after TWA data 104 is stored in memory 82, or on a periodic basis. Alarm unit 138 may generate an alarm signal based on a comparison of threshold data 106 to TWA data 104. In the illustrated example, threshold data 106 includes threshold value 166. Threshold value 166 may be a variable value that can be manually adjusted by an authorized user of programmer 24. In other examples, threshold value 166 may be determined based on an average of previously accumulated TWA data 104. In any case, alarm unit 138 may selectively output an alarm signal based on a comparison of threshold data 106 to TWA data 104. Processor 80 may, upon receiving the alarm signal, cause IMD 16 to emit an audible sound to alert the patient to seek immediate medical attention. Alternatively, processor 80 may transmit information to programmer 24 or access point 200 via telemetry module 88 in response to receiving the alarm signal.

Although TWA module 92 is illustrated in FIG. 7 as including Fourier transform unit 134 to process the sampled T-wave values in the frequency domain, it should be understood that TWA module 92, in some examples, may replace Fourier transform unit 134 with components, i.e., hardware and software components, for processing the T-wave samples in the time domain to determine TWA values. For example, TWA module 92 may include components for calculating the difference between samples of T-wave pairs, and determining TWA values based on the difference values. As previously described, TWA module 92 may, in some examples, calculate the difference values on a running basis to reduce the amount of data stored in memory 82.

FIGS. 8-11 are flow diagrams illustrating example methods that may be performed by one or more of IMD 16, programmer 24, or any other devices described herein, to monitor TWAs for patient 14. The flow diagrams of FIGS.

8-11 are described with respect to IMD 16 shown in FIG. 4 and programmer 24 shown in FIG. 5.

Figure 8:
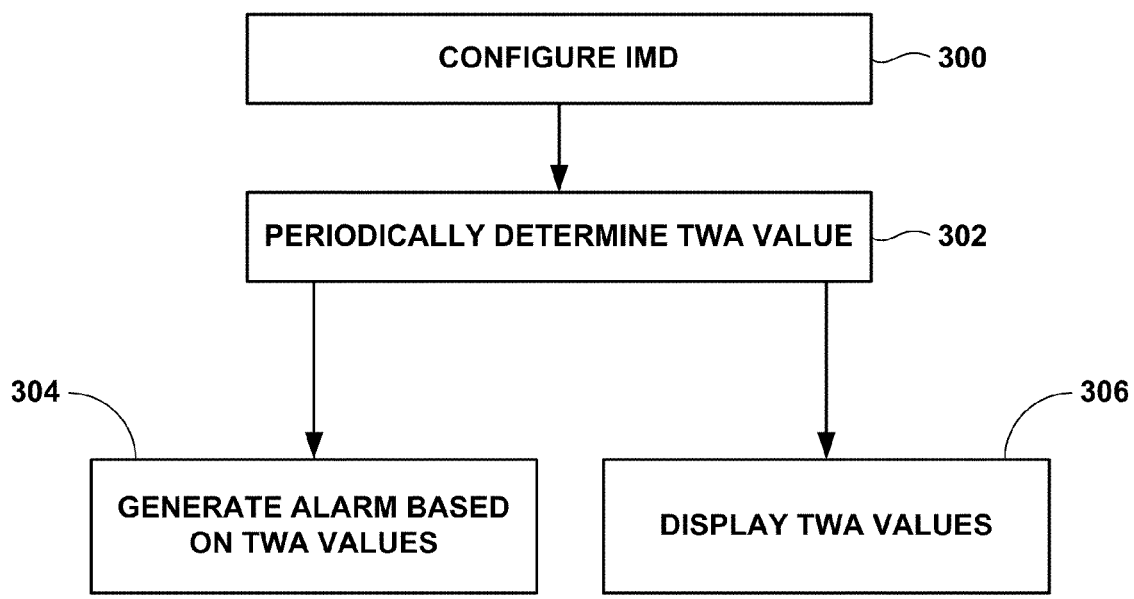
FIGS. 8-11 are flow diagrams illustrating example methods for monitoring TWAs.

FIG. 8 is a flow diagram illustrating an example method for measuring TWAs of patient 12. The first step in the example method shown in FIG. 8 is to configure IMD 16 (300). Configuring IMD 16 may, for example, include operating programmer 24 in a configuration mode to select an optimal sampling interval that may be used by IMD 16 to determine TWA values for the patient. A detailed description of an example method for selecting an optimal sampling interval is provided in FIG. 11. Configuring IMD 16 may also include, in some examples, interacting with programmer 24 to select values for operational parameters of IMD 16 via programmer 24.

When IMD 16 is configured, IMD 16 periodically determines TWA values for patient 14 in accordance with various embodiments of this disclosure (302). That is, IMD 16 generates EGM signals, e.g., far field EGM signals, samples the EGM signals over each T-wave for a plurality of beats in accordance with the optimal sampling interval determined during the configuration step, and determines TWA values based on the sampled data. A more detailed description for determining TWA values for the patient is provided in FIG. 9.

IMD 16, or another device in communication with IMD 16, may then, in some examples, generate an alarm based on a comparison of one or more of the TWA values to a corresponding threshold value (304). Programmer 24, or another device in communication with IMD 16, may additionally or alternatively display the TWA values determined in step 102 to an authorized user, e.g., as a trend (306). IMD 16 may transmit the TWA values to programmer 24 or another device periodically or upon interrogation. The programmer or other device may display the TWA values to a user of programmer 24 in a graphical format, such as the format shown in FIG. 18. Other formats are also contemplated such as a histogram, a table, chart, and the like.

Figure 9:
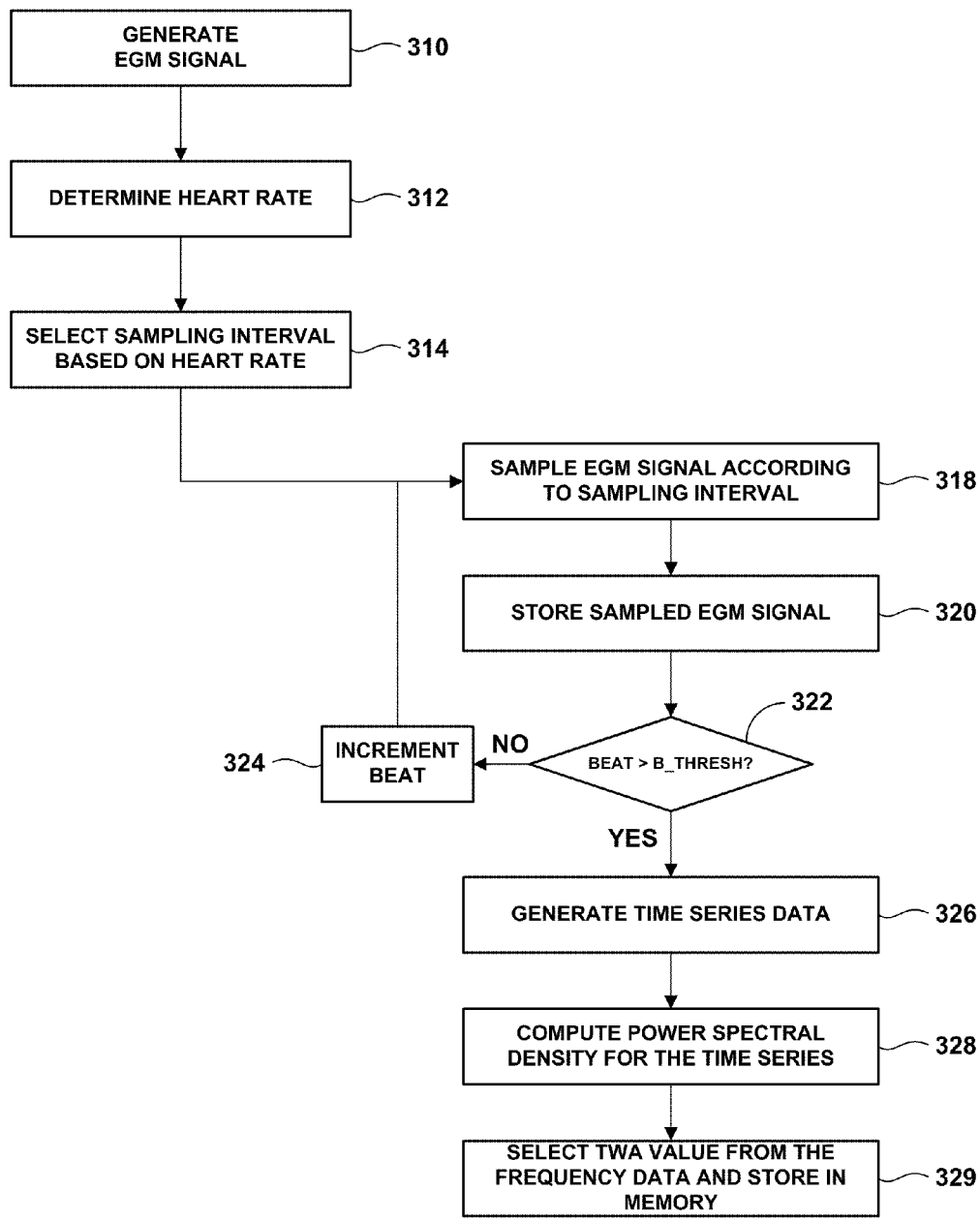

FIG. 9 is a flow diagram illustrating an example method that may be performed by IMD 16 to determine TWA values for patient 14. In various examples, the illustrated method may be performed by IMD 16, external programmer 24, any device described herein, or any combination thereof. For example, IMD 16 may generate EGM signals and process the EGM signals to determine TWA values in accordance with the method shown in FIG. 9. In another example, IMD 16 may generate EGM signals and send the EGM signals to external programmer 24 or server 204 for processing in the manner shown in FIG. 9. For purposes of illustration only, it will be assumed that the subsequent description that IMD 16 performs the method shown in FIG. 8. It will also be assumed that the illustrated method may be performed repeatedly over multiple periods of time, e.g., multiple times per day, on a daily basis, or the like.

Initially, IMD 16 generates an EGM signal (310). IMD 16 then determines the heart rate of the patient (312). In some examples, processor 80 may determine the heart rate of patient 14 by analyzing signals received from sensing module 86 using techniques described herein or known in the art.

TWA module 92 selects a sampling interval based on the heart rate determined in the previous step (314). In examples in which IMD 16 stores a plurality of sampling intervals that each correspond to a different heart rate, TWA module 92 selects the sampling interval that corresponds to the heart rate determined in the previous step. In other examples, IMD 16 may store a single sampling interval (or intervals) and "select" the sampling interval by adjusting the sampling interval based on the heart determined in the previous step.

After the sampling interval is selected, IMD 16 samples the far field EGM signal, referred to as the "EGM signal," according to the selected sampling interval (318). IMD 16 stores the sampled value in memory (320). As previously described, IMD 16 samples the EGM signal over each T-wave for a plurality of beats. This generally requires processing the EGM signal to detect the QRS complex or other fiducial point in the EGM signal and triggering the delay timer when QRS is detected. An example method for sampling the EGM signal is provided in FIG. 10. Accordingly, IMD 16 may compare a counter, i.e., "BEAT," to a threshold value, i.e., "B_THRESH," to determine when sampling is complete (322).

When BEAT is not greater than B_THRESH IMD 16, the BEAT variable is incremented (324) and steps 316, 318, and 320 are repeated. When BEAT is greater than B_THRESH, IMD 16 generates time series data from the EGM data stored in memory 82 (326). IMD 16 then computes the power spectral density for time series data (328). IMD 16 may perform a Fourier transform, such as an FFT or other DFT operation, on the time series data to generate the frequency data. Finally, IMD 16 selects the TWA value from the power spectral density (PSD) and stores the TWA value in memory (329). Specifically, IMD 16 may select the PSD for a frequency of approximately 0.5 cycles per beat as the TWA value.

In examples in which IMD 16 processes the sampled data in the time domain to determine the TWA value, IMD 16 may calculate differences between samples for T-wave pairs. IMD 16 may calculate the differences after sampling the EGM signal for the predetermined number of beats, i.e., B_THRESH, or may calculate the differences on a running a basis.

It should be understood that IMD 16 may execute the method illustrated in FIG. 9 on a repeated basis. For example, IMD 16 may execute the illustrated method on an hourly basis, daily basis, or in accordance with a programmable schedule. As another example, IMD 16 may execute the illustrated method when physiological conditions are met, such as when the patient exhibits a heart rate above a predetermined threshold value for a defined period of time.

Figure 10:
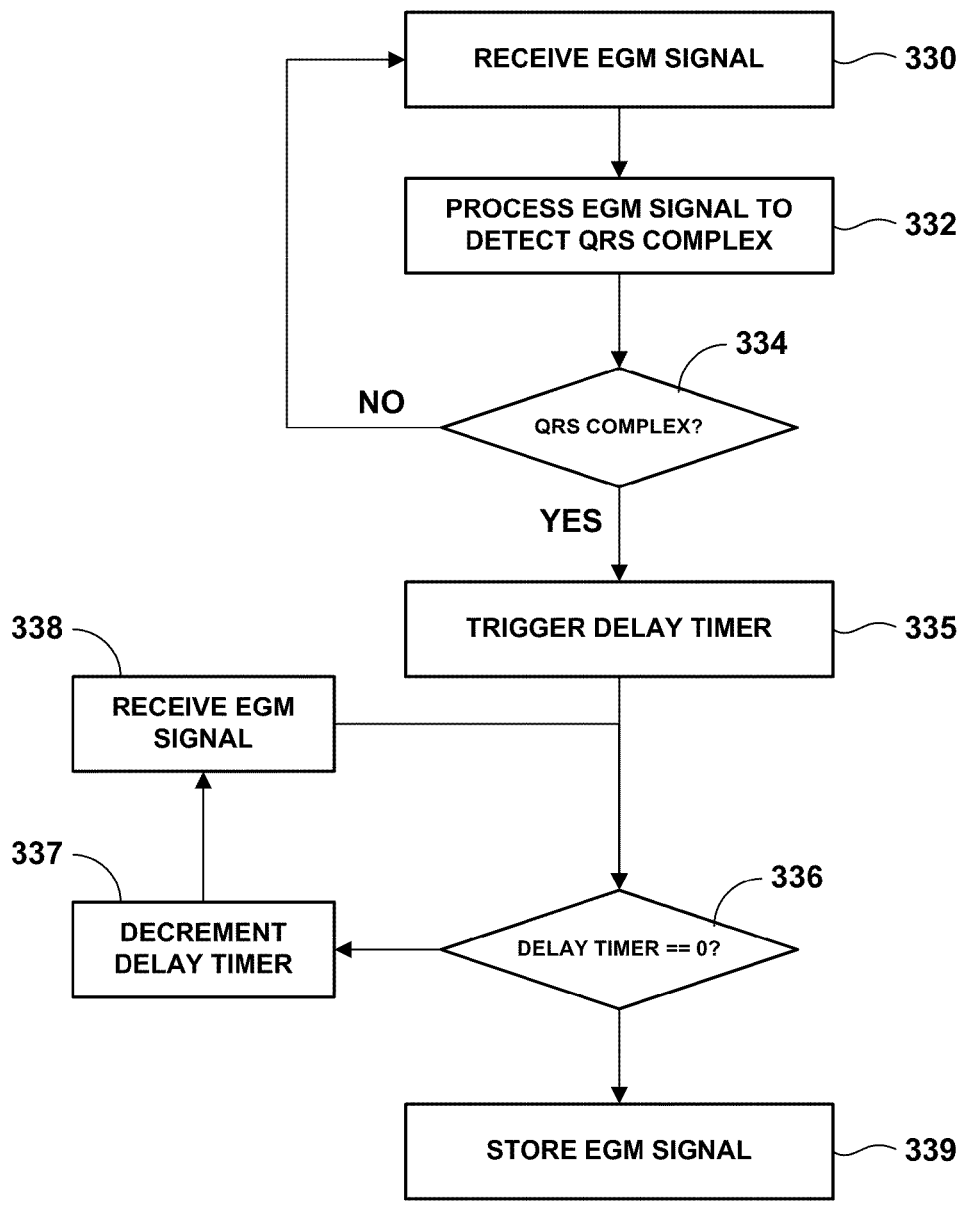

FIG. 10 is a flow diagram illustrating an example method for sampling the EGM signal in accordance with various embodiments of the invention. The method is described with respect to IMD 16 and, more particularly, TWA module 92 shown in FIG. 7.

First, sampling unit 130 receives an EGM signal from sensing module 86 (330). In this example, sampling unit 130 may receive the EGM signal as a substantially continuous stream of data points. Sampling unit 130 or, more particularly, QRS unit 170 processes the stream of EGM data points to detect a QRS complex (332). In some examples, QRS unit 170 may buffer a series of data points and process the data points within the buffer to detect a QRS complex or other fiducial point of the EGM signal.

Sampling unit 130 determines whether to sample the EGM signal or continue monitoring the EGM signal based on detection of a QRS complex (334). When sampling unit 130 does not detect a QRS complex, IMD 16 repeats steps 330 and 332. However, when sampling unit 130 does detect a QRS complex, sampling unit 130 triggers a delay timer (335). The delay timer, in this example, may be a counter for sampling the EGM signal at the correct time. The delay timer, i.e., counter, may be loaded with an integer value stored in memory 82. The integer value corresponds to the number of data points in an interval between the onset of the QRS complex and a point over the subsequent T-wave.

Delay unit 172 determines when to sampling the EGM signal based on the value of the delay timer (336). When the delay timer has not expired, i.e., is not equal to zero, delay unit 172 decrements the delay timer (337) and receives the next data point of the EGM signal (338). Delay unit 172 repeats step 336-338 until the delay timer reaches a value of zero.

When delay timer reaches a value of zero, sampling unit 130 stores the EGM signal (339) in memory 82. As previously described, the delay timer is selected so that the data point of the EGM signal that is stored in memory is an amplitude value of the T-wave following the detected QRS complex.

In accordance with the techniques described in this disclosure, the steps of the method illustrated in FIG. 10 are repeated for a plurality of beats so that a TWA value can be determined from the T-wave amplitude values stored in memory. In examples in which the EGM is sampled a plurality of times per beat, multiple different delay timers may be triggered (335) and decremented (337), and multiple values of the EGM signal may be stored (339).

Figure 11:
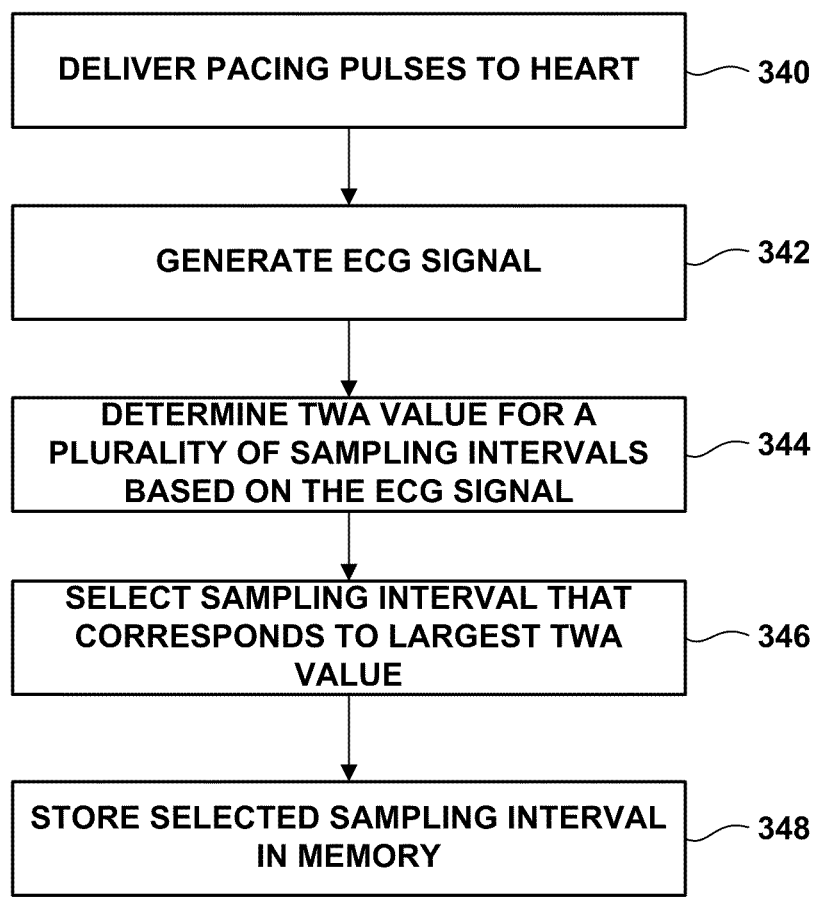

FIG. 11 illustrates an example method for determining a sampling interval for use in determining TWA values for patient 14 in accordance with the described techniques. In general, the illustrated method may be performed by programmer 24, but other methods executed by IMD 16, a combination of both programmer 24 and IMD 16, or any one or more devices described herein, are also contemplated. In any case, it will be assumed for the subsequent description that programmer 24 performs the method shown in FIG. 11. It will also be assumed that the illustrated method may be performed repeatedly to determine sampling intervals that correspond to different heart rates.

Generally, an authorized user of programmer 24 may operate programmer 24 in a configuration mode during implantation of IMD 16 within patient 14. During the implantation of IMD 16, epicardial leads and/or patch electrodes may be attached to the skin of patient 14 or generating a 12 lead ECG signal. Programmer 24 may be configured to interface with these medical leads or a clinician may interact with programmer 24 to control an external stimulator coupled to the medical leads. In particular, the clinician interacts with programmer 24 to deliver pacing pulses to the heart of patient 14 (340). The clinician may use programmer 24 to manually select the pacing rate. Alternatively, the pacing rate may be a predetermined value loaded into programmer 24 prior to the implant procedure.

Programmer 24 generates an ECG (342), e.g., a 12 lead ECG signal, while pacing the heart of patient 14. Programmer 24 then determines a TWA value for a plurality of sampling intervals based on the ECG signal (344). Programmer 24 may utilize digital signal processing techniques to determine each of the TWA values. In examples in which IMD 16 executes the method illustrated in FIG. 11, IMD 16 may determine each of the TWA values using the techniques described in this disclosure. For example, programmer 24 may determine the TWA values by sampling each of a plurality of T-waves every 5 ms over a 150 ms T-wave window. In any case, each of the TWA values is determined for each of a plurality of different sampling intervals. In some examples, programmer 24 may determine 30 or more TWA values that each correspond to a different sampling interval.

Programmer 24 then selects the sampling interval from the plurality of sampling intervals that corresponds to the largest TWA value (346). Programmer 24 stores the sampling interval in memory 82 of IMD 16 (348). For example, programmer 24, upon completion of the illustrated method, may transmit the sampling interval to IMD 16 via telemetry module 116.

Figure 12:
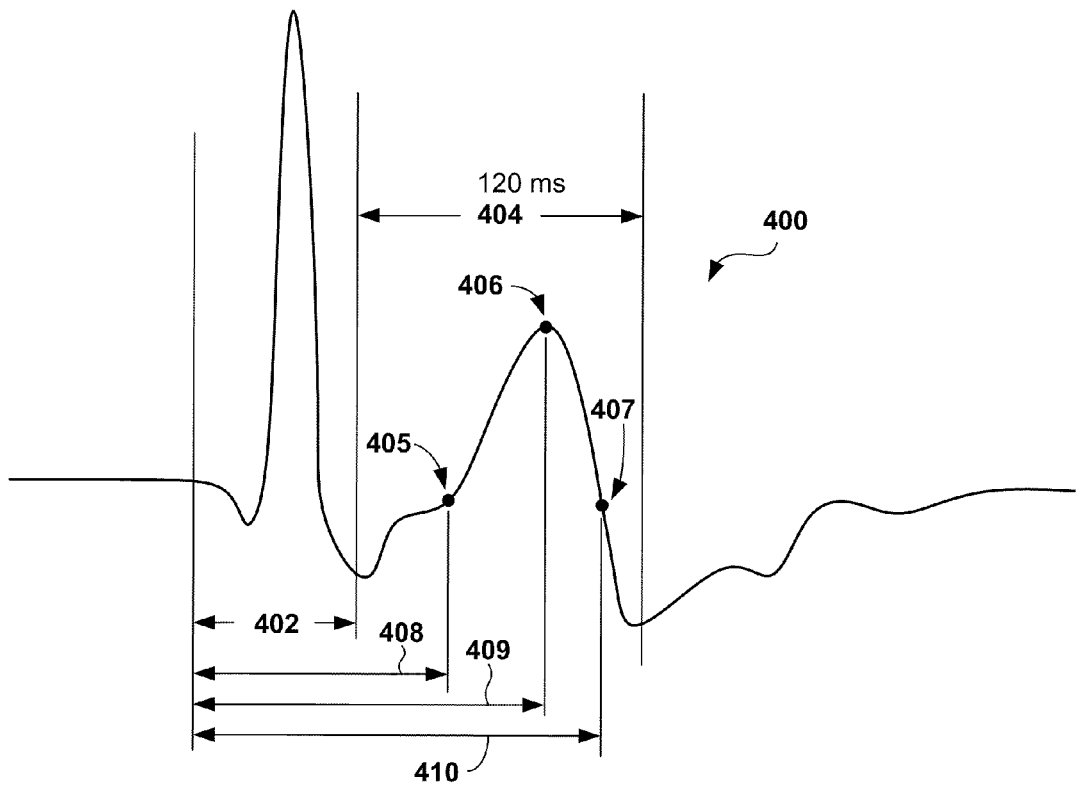
FIG. 12 illustrates one heart beat of an example electrogram (EGM) signal.

FIG. 12 illustrates an example EGM signal 400. In particular, FIG. 12 illustrates example EGM signal 400 for a single heart beat. The purpose of example EGM signal 400 is to illustrate example cardiac waveforms and EGM signal parameters used by IMD 16 to determine TWA values.

In the example illustrated in FIG. 12, EGM signal 400 includes QRS complex 402 and T-wave 404. T-wave 404 may be approximately 120 ms. Accordingly, a T-wave window used during the configuration mode to determine an optimal sampling interval may also be approximately 120 ms. In other examples, a larger T-wave window may be used. For example, a T-wave window may be used that is approximately 250 ms.

FIG. 12 also illustrates various example sampling points 405-407 that may be used by IMD 16 to determine TWA values. Each of sample points 405-407 corresponds to one of sampling intervals 408-410. Sampling intervals 408-410 define intervals between the onset of QRS complex 402 and the corresponding one of sampling points 405-407, respectively. In the illustrated example, sampling interval 409 represents the optimal sampling interval.

Although three example sample points 408-410 are shown in FIG. 12, it should be understood that one or more sample points may be used for determining TWA values in accordance with the described techniques. In some examples, IMD 16 determine TWA values for patient 14 using a single sampling interval and, thus, store a single data point in memory for each of a plurality of beats. In other examples, however, IMD 16 may determine TWA values using more than one sampling interval. In accordance with the described techniques, it should be understood that the number of sampling intervals used for determining TWA values is a function of the memory of IMD 16.

Figure 13:
FIG. 13 illustrates multiple heart beats of an example EGM.

FIG. 13 illustrates an example EGM signal 420 that includes multiple heart beats 422A-F. In operation, IMD 16 may sample EGM signal 420 once for each of beats 422A-F. In accordance with the described techniques, IMD 16 may store in memory 82 a single T-wave amplitude value for each of beats 422A-F, and determine a TWA value based on those stored T-wave amplitude values.

Figure 14:
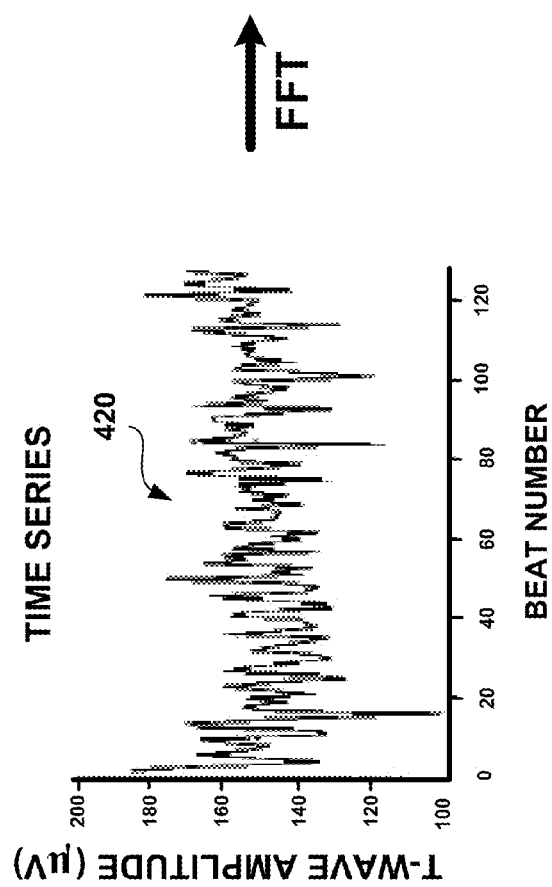
FIG. 14 is a graph that illustrates an example time series of T-wave amplitude values.

FIG. 14 is a graph that illustrates example time series data 420. Time series data 420 is a time ordered sequence of the data sampled from the EGM signal for a plurality, e.g., 128, consecutive beats. In FIG. 14, the beat number is plotted along the horizontal axis and the amplitude of the sampled data is plotted along the vertical axis.

Figure 15:
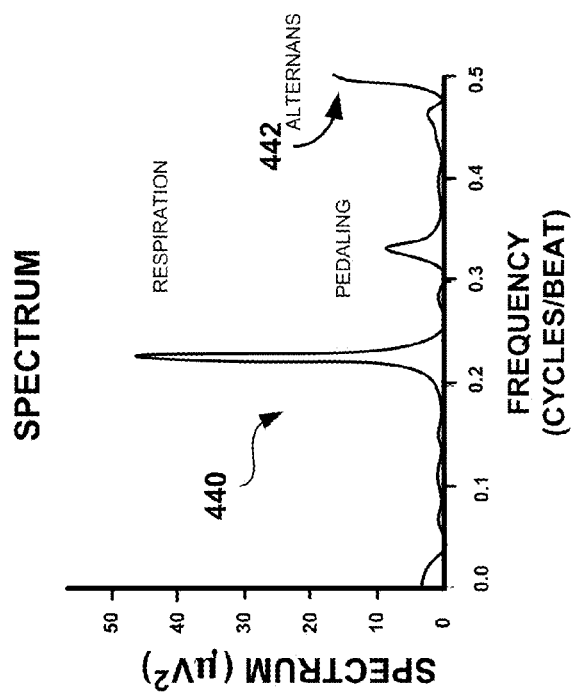
FIG. 15 is a graph that illustrates an example frequency spectrum of the time series shown in FIG. 14.

FIG. 15 is a graph that illustrates the power spectral density 440 of time series data 420. In FIG. 15, frequency is plotted along the horizontal axis and the power spectral density is plotted along the vertical axis ($\mu V^2$). The power spectral density signal 440 includes three spikes located at different frequencies. The spike labeled 442 is located at approximately 0.5 cycles per beat. The PSD value 442, e.g., the power of the time series data 420 at approximately 0.5 cycles per beat, may be used as the TWA value.

Figure 16:
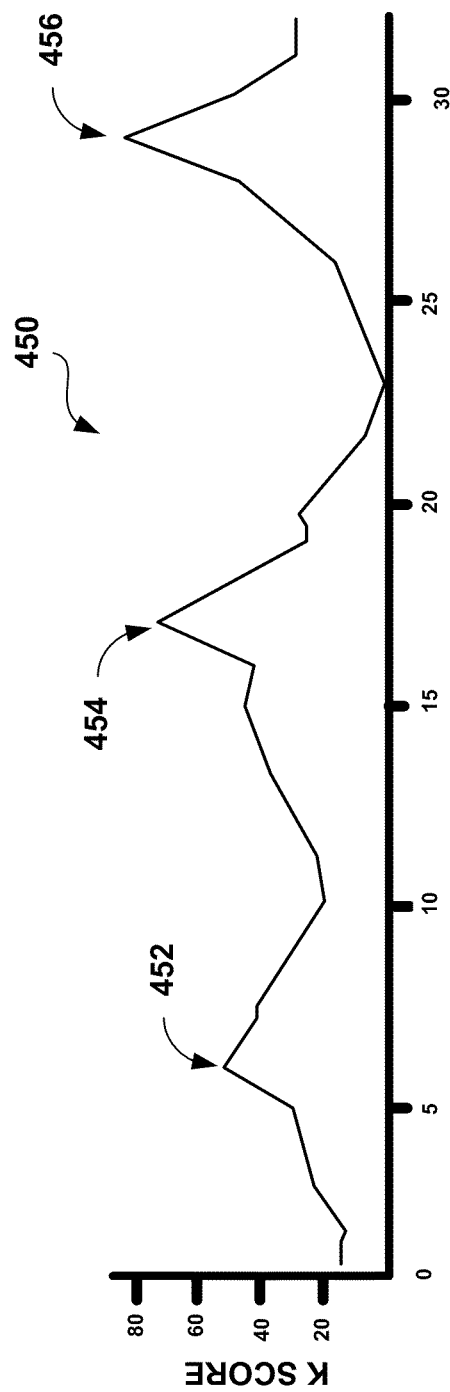
FIG. 16 is a graph that illustrates an example relationship between TWA values, or K values, and the sampling interval for an EGM signal.

FIG. 16 is a graph that illustrates K scores 450 for different sampling points over a T-wave segment in each of a plurality of beats, e.g., determined during configuration according to the techniques described herein (e.g., FIG. 11). The K score is a value that corresponds to a TWA value. Thus, the graph in FIG. 16 illustrates different TWA values or K scores obtained using different sampling intervals over a plurality of beats.

Three distinct peaks 452, 454 and 456 are shown in FIG. 16. A first peak 452 is located at the 6th sample point and a second peak 454 is located at the 17th sample point. A third peak 456 that has the largest TWA value of the three peaks is located at the 29th sample point. Accordingly, programmer 24 may select the sampling interval that corresponds to the 29th sample point as the optimum sampling interval for determining TWA values for the patient.

FIG. 17 is a graph that illustrates an example trend diagram of TWA values 460 for a patient. The graph shown in FIG. 17 may be displayed to a physician, clinician, or other medical personnel to aid in making clinical decisions for the patient. As indicated by the arrow in FIG. 17, an increase in the TWA value corresponds to an increase in likelihood that the patient will experience a VT/VF episode.

In the example illustrated in FIG. 17, the time period is plotted along the horizontal axis in days/months. In other examples, however, the time period may be plotted to a different scale, such as hours.

Various examples have been described. These and other examples are within the scope of the following claims. For example, one of ordinary skill in the art will appreciate that various modifications may be made to the described examples without departing from the scope of the claims.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

The invention claimed is:

1. A method comprising:
generating an electrocardiogram (ECG) signal of a patient via one or more medical leads attached to the patient;
sampling the ECG signal at a plurality of sample times over each of a plurality of T-waves for each of a plurality of beats to obtain a sample point from each of the T-waves for each of the sample times;
determining a plurality of ECG-based T-wave alternans (TWA) values, wherein each of the ECG-based TWA values is determined from the sample points from each of the T-waves associated with a respective sample time during each of the T-waves;
determining one of the plurality of sample times associated with a largest one of the ECG-based TWA values;
selecting an interval based on the sample time associated with the largest one of the plurality of ECG-based TWA values;
generating an electrogram (EGM) signal of the patient using an implantable medical device;
storing one or more samples of the EGM signal per heartbeat of the patient for a plurality of heartbeats, wherein for each heartbeat a stored sample is an amplitude of a T-wave that occurs after a fiducial point of the EGM signal by an amount of time equal to the selected interval; and
determining an EGM-based TWA value based on the T-wave amplitudes of the EGM signal.

2. The method of claim 1, wherein storing and determining comprises storing and determining by the implantable medical device.

3. The method of claim 1, wherein the fiducial point is a QRS complex.

4. The method of claim 1, further comprising:
selecting a plurality of intervals based on sample times associated with the largest ECG-based TWA values for different heart rates;
determining a heart rate of the patient based on the EGM signal; and
selecting one of the plurality of intervals based on the determined heart rate.

5. The method of claim 1, further comprising:
determining a heart rate of the patient based on the EGM signal; and
automatically adjusting the interval based on the heart rate.

6. The method of claim 1, further comprising generating an alert if the EGM-based TWA value exceeds a threshold.

7. The method of claim 1, further comprising:
repeating, over multiple time periods, the generating, storing, and determining to determine a plurality of EGM-based TWA values; and
displaying the EGM-based TWA values as a trend.

8. The method of claim 1, wherein determining the EGM-based TWA value comprises:
creating a time series of the T-wave amplitude values of the EGM signal;
computing a power spectrum of the time series; and
selecting the power spectrum value at a particular frequency as the EGM-based TWA value.

9. The method of claim 1, wherein determining the EGM-based TWA value comprises:
computing a difference between samples of consecutive T-waves of the EGM signal; and
determining the EGM-based TWA value based on the difference values.

10. The method of claim 1, wherein storing one or more samples of the EGM signal comprises storing fifty samples or less of the EGM signal per heart beat of the patient.

11. The method of claim 1, wherein storing one or more samples of the EGM signal comprises storing ten samples or less of the EGM signal per heartbeat of the patient.

12. A system comprising:
at least one external device that:

generates an electrocardiogram (ECG) signal of a patient via one or more medical leads attached to the patient;

samples the ECG signal at a plurality of sample times over each of a plurality of T-waves for each of a plurality of beats to obtain a sample point from each of the T-waves for each of the sample times;

determines a plurality of ECG-based T-wave alternans (TWA) values, wherein each of the ECG-based TWA values is determined from the sample points from each of the T-waves associated with a respective sample time during each of the T-waves;

determines one of the plurality of sample times associated with a largest one of the ECG-based TWA values; and selects an interval based on the sample time associated with the largest one of the plurality of ECG-based TWA values;

one or more electrodes;

an implantable medical device coupled to the electrodes comprising a sensing module that senses an electrogram (EGM) signal of the patient via the electrodes;

a memory; and a T-wave alternans (TWA) module that stores one or more samples of the EGM signal per heartbeat of the patient for a plurality of heartbeats in the memory, wherein for each heartbeat a stored sample is an amplitude of a T-wave that occurs after a fiducial point of the EGM signal by an amount of time equal to the selected interval, and determines an EGM-based TWA value based on the stored T-wave amplitudes of the EGM signal.

13. The system of claim 12, wherein the memory is a memory of implantable medical device.

14. The system of claim 12, wherein the implantable medical device comprises at least one of a monitor, a pacemaker, a cardioverter, or a defibrillator.

15. The system of claim 12, wherein the implantable medical device comprises the TWA module.

16. The system of claim 12, wherein the fiducial point is a QRS complex.

17. The system of claim 12, wherein the at least one external device selects a plurality of intervals based on sample times associated with the largest ECG-based TWA values for different heart rates, wherein the TWA module determines a heart rate of the patient, and wherein the TWA module selects one of the plurality of intervals based on the determined heart rate.

18. The system of claim 12, wherein the TWA module determines a heart rate of the patient, and automatically adjusts the interval based on the heart rate.

19. The system of claim 12, wherein the TWA module generates an alert if the EGM-based TWA value exceeds a threshold.

20. The system of claim 12, wherein the TWA module repeats, over multiple time periods, the sampling and determining to determine a plurality of EGM-based TWA values, the system further comprising a display to display the EGM-based TWA values as a trend.

21. The system of claim 12, wherein the TWA module creates a time series of the T-wave amplitude values of the EGM signal, computes a power spectrum of the time series, and selects the power spectrum value at a particular frequency as the EGM-based TWA value.

22. The system of claim 12, wherein the TWA module computes a difference between samples of consecutive T-waves of the EGM signal, and determines the EGM-based TWA value based on the difference values.

23. The system of claim 12, wherein the TWA module stores fifty or fewer samples the EGM signal per heart beat of the patient.

24. The system of claim 12, wherein the TWA module stores ten or fewer samples the EGM signal per heartbeat of the patient.

25. A system comprising:
at least one external device that:
generates an electrocardiogram (ECG) signal of a patient via one or more medical leads attached to the patient;

samples the ECG signal at a plurality of sample times over each of a plurality of T-waves for each of a plurality of beats to obtain a sample point from each of the T-waves for each of the sample times;

determines a plurality of ECG-based T-wave alternans (TWA) values, wherein each of the ECG-based TWA values is determined from the sample points from each of the T-waves associated with a respective sample time during each of the T-waves;

determines one of the plurality of sample times associated with a largest one of the ECG-based TWA values;

selects an interval based on the sample time associated with the largest one of the plurality of ECG-based TWA values;

means for generating an electrogram (EGM) signal of the patient using an implantable medical device;

means for storing one or more samples of the EGM signal per heartbeat of the patient for a plurality of heart beats, wherein for each heartbeat a stored sample is an amplitude of a T-wave that occurs after a fiducial point of the EGM signal by an amount of time equal to the selected interval; and means for determining an EGM-based TWA value based on the T-wave amplitudes of the EGM signal.

26. A non-transitory computer-readable storage medium comprising instructions that cause one or more processors to:
generate an electrocardiogram (ECG) signal of a patient via one or more medical leads attached to the patient;

sample the ECG signal at a plurality of sample times over each of a plurality of T-waves for each of a plurality of beats to obtain a sample point from each of the T-waves for each of the sample times;

determine a plurality of ECG-based T-wave alternans (TWA) values, wherein each of the ECG-based TWA values is determined from the sample points from each of the T-waves associated with a respective sample time during each of the T-waves;

determine one of the plurality of sample times associated with a largest one of the ECG-based TWA values;

select an interval based on the sample time associated with the largest one of the plurality of ECG-based TWA values;

generate an electrogram (EGM) signal of the patient;

store one or more samples of the EGM signal per heartbeat of the patient for a plurality of heart beats, wherein for each heartbeat a stored sample of the EGM signal is an amplitude of a T-wave that occurs after a fiducial point of the EGM signal by an amount of time equal to the selected interval; and determine an EGM-based TWA value based on the T-wave amplitudes of the EGM signal.

* * * * *

UNITED STATES PATENT AND TRADEMARK OFFICE
CERTIFICATE OF CORRECTION

| | | |
|---|---|---|
| PATENT NO. | : 8,634,903 B2 | Page 1 of 1 |
| APPLICATION NO. | : 12/610062 | |
| DATED | : January 21, 2014 | |
| INVENTOR(S) | : Vinod Sharma et al. | |

It is certified that error appears in the above-identified patent and that said Letters Patent is hereby corrected as shown below:

In the claims

Col. 28, line 62, delete "signal per heart beat of the patient" and insert in place thereof
-- signal per heartbeat of the patient --;

Col. 30, line 4, delete "fifty or fewer samples the EGM" and insert in place thereof
-- fifty or fewer samples of the EGM --;

Col. 30, line 4, delete "signal per heart beat of the patient" and insert in place thereof
-- signal per heartbeat of the patient --;

Col. 30, line 7, delete "ten or fewer samples the EGM" and insert in place thereof
-- ten or fewer samples of the EGM --;

Col. 30, line 58, delete "plurality of heat beats, wherein" and insert in place thereof
-- plurality of heartbeats, wherein --.

Signed and Sealed this
Ninth Day of February, 2016

Michelle K. Lee
*Director of the United States Patent and Trademark Office*